(12) United States Patent
Kobayashi et al.

(10) Patent No.: US 10,519,473 B2
(45) Date of Patent: Dec. 31, 2019

(54) MICROORGANISM HAVING MULTIPLE GENES ENCODING PHA SYNTHASE AND METHOD FOR PRODUCING PHA USING SAME

(71) Applicant: KANEKA CORPORATION, Osaka-shi (JP)

(72) Inventors: Shingo Kobayashi, Takasago (JP); Rina Aoki, Takasago (JP); Tetsuya Minami, Settsu (JP); Hisashi Arikawa, Takasago (JP); Keiji Matsumoto, Osaka (JP)

(73) Assignee: KANEKA CORPORATION, Osaka-shi (JP)

( * ) Notice: Subject to any disclaimer, the term of this patent is extended or adjusted under 35 U.S.C. 154(b) by 0 days.

(21) Appl. No.: 15/129,726

(22) PCT Filed: Mar. 27, 2015

(86) PCT No.: PCT/JP2015/001795
§ 371 (c)(1),
(2) Date: Sep. 27, 2016

(87) PCT Pub. No.: WO2015/146195
PCT Pub. Date: Oct. 1, 2015

(65) Prior Publication Data
US 2017/0198313 A1    Jul. 13, 2017

(30) Foreign Application Priority Data

Mar. 28, 2014    (JP) .................................. 2014-067674

(51) Int. Cl.
*C12P 7/62* (2006.01)
*C12N 9/10* (2006.01)
*C12N 9/88* (2006.01)

(52) U.S. Cl.
CPC ............ *C12P 7/625* (2013.01); *C12N 9/1029* (2013.01); *C12N 9/88* (2013.01); *C12Y 203/01* (2013.01); *C12Y 402/01017* (2013.01)

(58) Field of Classification Search
None
See application file for complete search history.

(56) References Cited

U.S. PATENT DOCUMENTS

| 2009/0130731 A1 | 5/2009 | Maruyama |
| 2011/0091948 A1 | 4/2011 | Murakami et al. |
| 2013/0071892 A1 | 3/2013 | Fukui et al. |

FOREIGN PATENT DOCUMENTS

| JP | 6-157878 A | 6/1994 |
| JP | 8-510498 A | 11/1996 |
| JP | 2004-250629 A | 9/2004 |
| WO | WO 94/28070 A1 | 12/1994 |
| WO | WO 02/50156 A2 | 6/2002 |
| WO | WO 02/50156 A3 | 6/2002 |
| WO | WO 2009/145164 A1 | 12/2009 |
| WO | WO 2011/105379 A1 | 9/2011 |

OTHER PUBLICATIONS

Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Kisselev L., Polypeptide release factors in prokaryotes and eukaryotes: same function, different structure. Structure, 2002, vol. 10: 8-9.*
Fukui et al. Co-expression of polyhydroxyalkanoate synthase and (R)-enoyl-CoA hydratase genes of Aeromonas caviae establishes copolyester biosynthesis pathway in *Escherichia coli*. FEMS Microbiology Letters 170 (1999) 69-75.*
Mifune et al. Engineering of pha operon on Cupriavidus necator chromosome for efficient biosynthesis of poly(3-hydroxybutyrate-co-3-hydroxyhexanoate) from vegetable oil., Polymer Degradation and Stability (2010), 95: 1305-1312.*
Extended European Search Report dated Jul. 18, 2017 in Patent Application No. 15769649.3.
English translation of International Preliminary Report on Patentability and Written Opinion dated Oct. 13, 2016 in PCT/JP2015/001795.
English translation International Search Report dated Jun. 23, 2015 in PCT/2015/001795.
Wing-Hin Lee, et al., "Biosynthesis of polyhydroxyalkanoate copolymers from mixtures of plant oils and 3-hydroxyvalerate precursors" Bioresource Technology, vol. 99, 2008, pp. 6844-6851.
Hiromi Matsusaki, et al., "Cloning and Molecular Analysis of the Poly(3-hydroxybutyrate) and Poly(3-hydroxybutyrate-co-3-hydroxyalkanoate) Biosynthesis Genes in *Pseudomonas* sp. Strain 61-3" Journal of Bacteriology, vol. 180, No. 24, 1998, pp. 6459-6467.

(Continued)

*Primary Examiner* — Iqbal H Chowdhury
(74) *Attorney, Agent, or Firm* — Oblon, McClelland, Maier & Neustadt, L.L.P.

(57) ABSTRACT

A PHA copolymer which is slowly crystallized is improved in crystallization speed to improve the melt workability of the PHA copolymer in working such as injection molding, film molding, blow molding, fiber spinning, extrusion foaming or bead foaming, thereby improving the resultant articles in productivity. A method for the improvement is a method for producing a PHA mixture, including the step of culturing a microorganism having both of a gene encoding a PHA synthase that synthesizes a copolymer PHA (A) and that is derived from the genus *Aeromonas*, and a gene encoding a PHA synthase that synthesizes a PHA (B) different in melting point from the copolymer PHA (A) by 10° C. or more to produce, in a cell of the microorganism, two or more PHAs different in melting point from one another by 10° C. or more simultaneously.

12 Claims, 4 Drawing Sheets
Specification includes a Sequence Listing.

(56) References Cited

OTHER PUBLICATIONS

Arnulf Timm et al., "Formation of blends of various poly(3-hydroxyalkanoic acids) by a recombinant strain of Pseudomonas oleovorans" Applied Microbiology and Biotechnology, vol. 33, 1990, pp. 296-301.

Matthias Liebergesell, et al., "Analysis of polyhydroxyalkanoic acid-biosynthesis genes of anoxygenic phototrophic bacteria reveals synthesis of a polyester exhibiting an unusual composition" Applied Microbiology and Biotechnology, vol. 40, 1993, pp. 292-300.

Kawalprest K. Aneja, et al., Altered composition of Ralstonia eutropha poly(hydroxyalkanoate) through expression of PHA synthase from Allochromatium vinosum ATCC 35206, Biotechnology Letter, vol. 31, 2009, pp. 1601-1612.

Jian Sun, et al., "Production of P(3-hydroxybutyrate-co-3-hydroxyhexanoate-co-3-hydroxyoctanoate) Terpolymers Using a Chimeric PHA Synthase in Recombinant Ralstonia eutropha and Pseudomonas putida" Biosci. Biotechnol. Biochem., vol. 74, No. 8, 2010, pp. 1716-1718.

Ken'ichiro Matsumoto, et al., "Chimeric Enzyme Composed of Polyhydroxyalkanoate (PHA) Syntheses from Ralstonia eutropha and Aeromonas caviae Enhances Production of PHAs in Recombinant *Escherichie coli*" Biomacromolecules, vol. 10, No. 4, 2009, pp. 682-685.

Rand et al, "Genome sequence and analysis of *Escherichia coli* production strain LS5218", *Metabolic Engineering Communications*, 2017, vol. 5, pp. 78-83.

Jun Mifune, et al; "Targeted engineering of Cupriavidus necator chromosome for biosynthesis of poly(3-hydroxybutyrate-do-3-hydroxyhexanoate) from vegetable oil[1]"; Can. J. Chem. vol. 86: pp. 621-627; 2008.

Japanese Office Action dated Jan. 15, 2019, in Japanese Patent Application No. 2016-510051 (with English Translation).

Database GenBank [online], Accession No. WP_011615085, <http://www.ncbi.nlm.nih.gov/protein/499934351?report=genbank&log$=protalign&blast_rank=1&RID=R9Z8762S014>, Jul. 18, 2013 uploaded, [retrieved on Jun. 9, 2015], Definition: poly-beta-hydroxybutyrate polymerase [*Cupriavidus necator*]., entire text.

* cited by examiner

[Fig. 1]
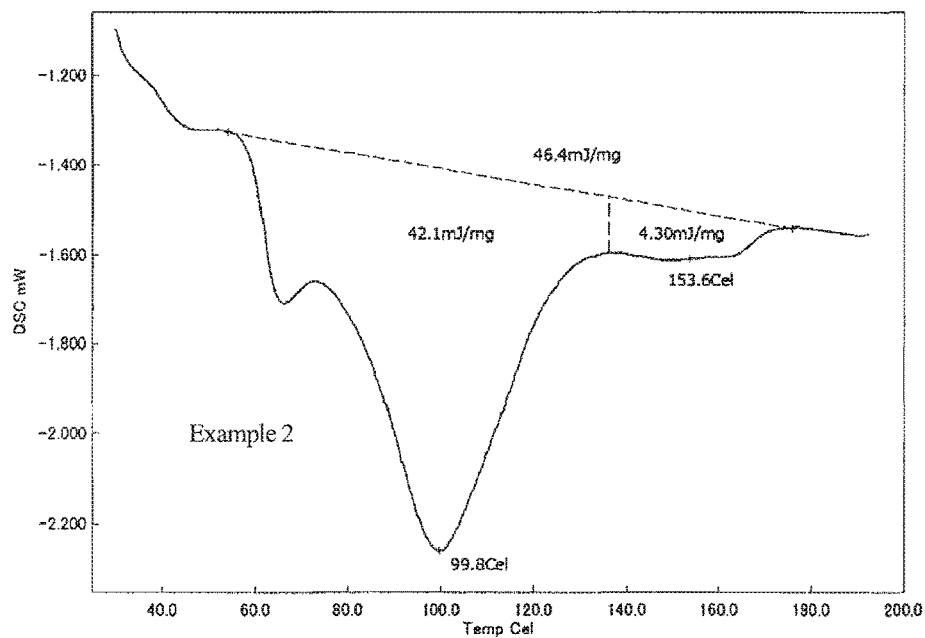
[Fig. 2]
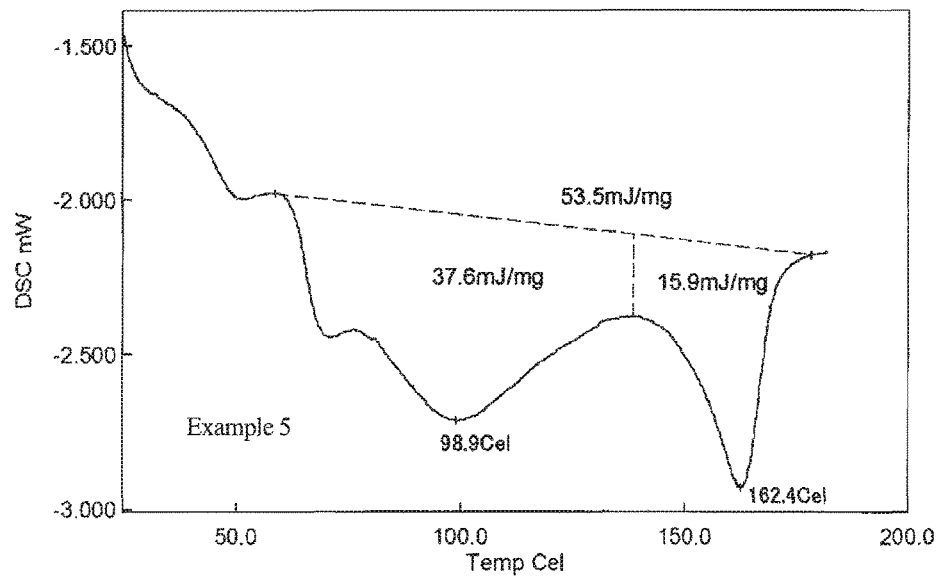

[Fig. 3]
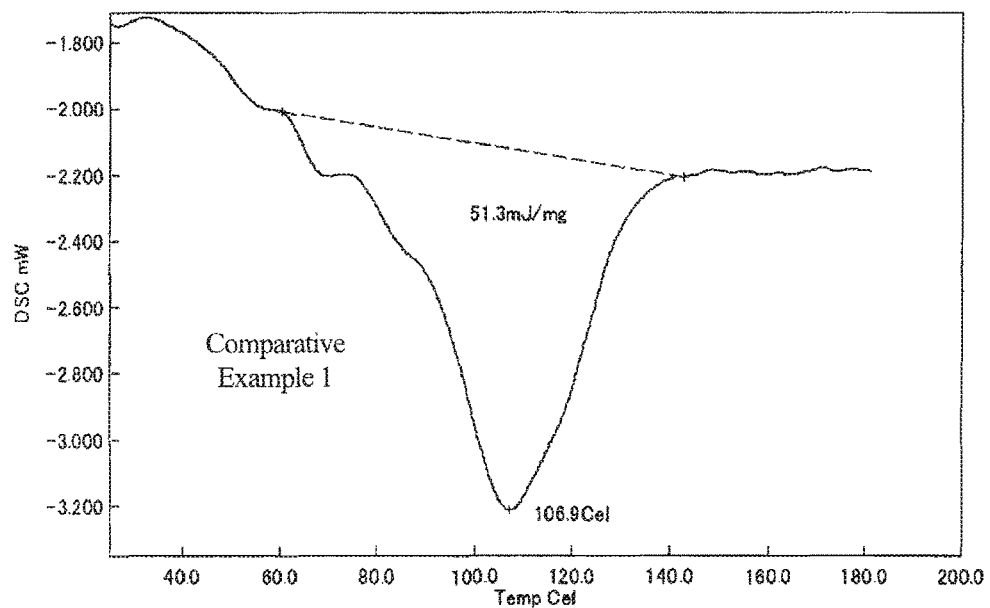
[Fig. 4]
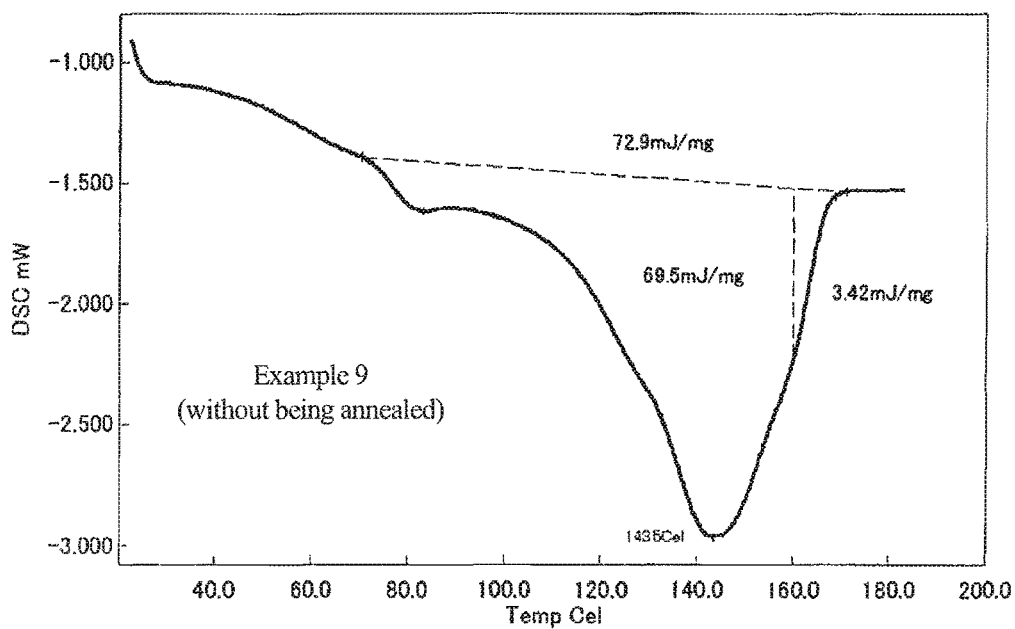

[Fig. 5]
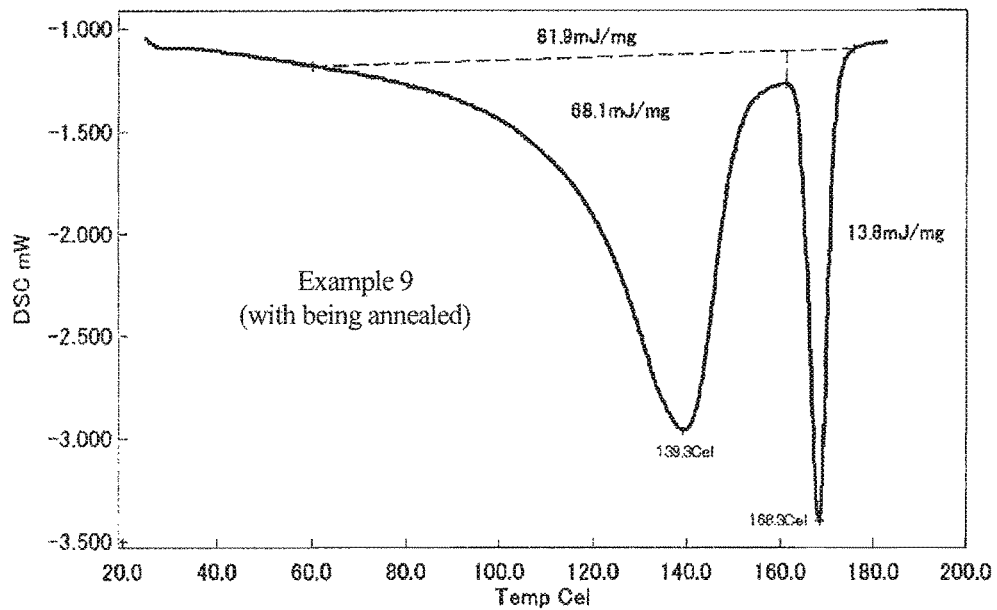
[Fig. 6]
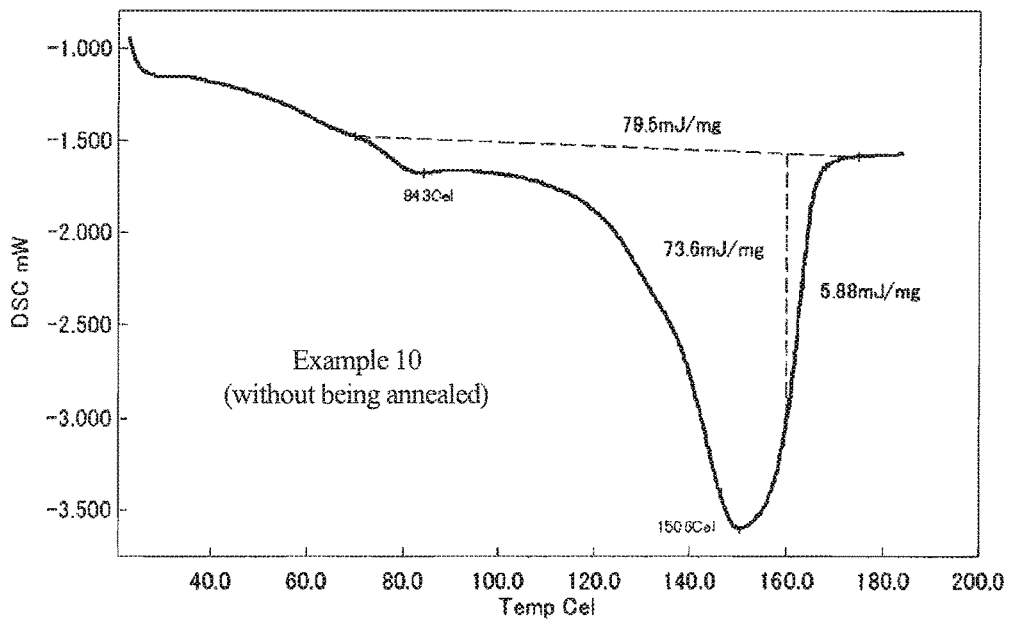

[Fig. 7]
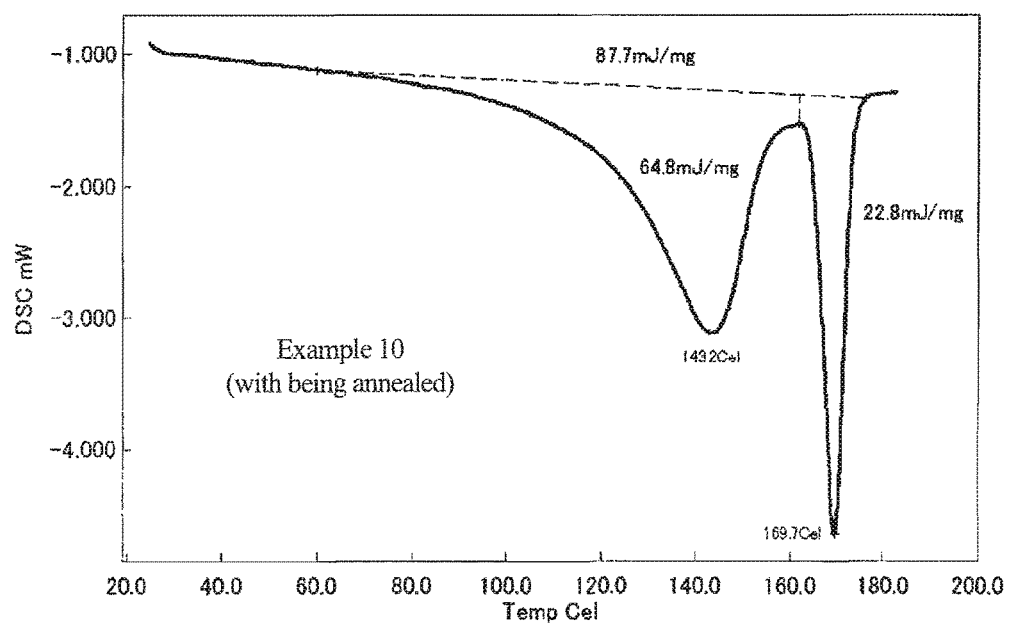
[Fig. 8]
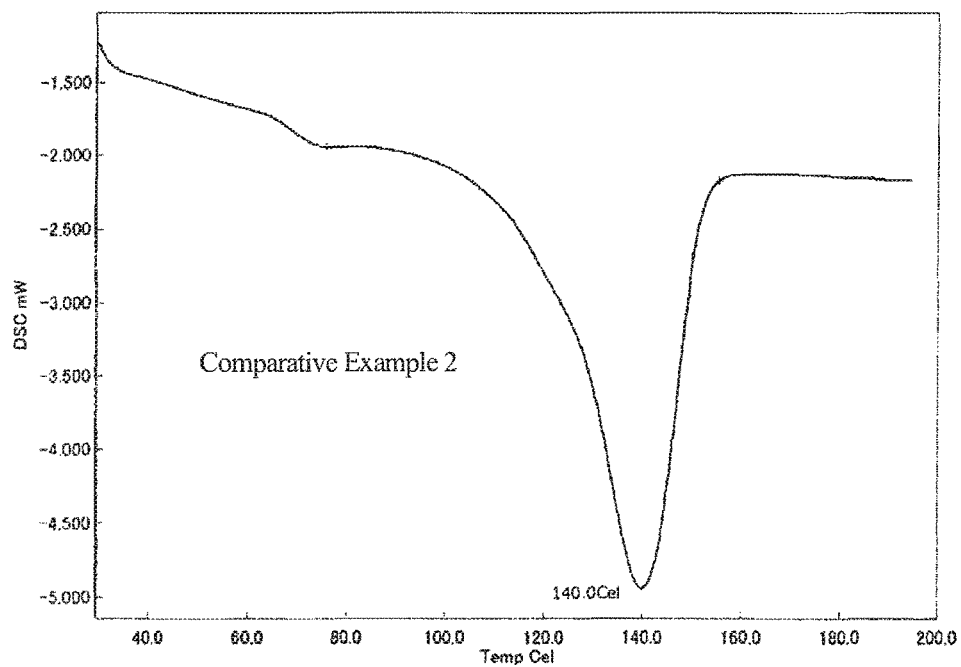

MICROORGANISM HAVING MULTIPLE GENES ENCODING PHA SYNTHASE AND METHOD FOR PRODUCING PHA USING SAME

TECHNICAL FIELD

The present invention relates to a microorganism for producing, in a cell thereof, two or more PHAs different in melting point from one another; and a method for producing a PHA high in crystallization/solidification speed, using the microorganism.

BACKGROUND ART

A polyhydroxyalkanoic acid (abbreviated hereinafter to a "PHA") is a thermoplastic polyester produced and stored as an energy storing substance inside cells of many microorganism species. The PHA, which is produced from various natural carbon sources by microorganisms, is completely biodegraded by a microorganism in the earth or in water to be taken into a carbon cycle process in the natural world. It can be therefore stated that the PHA is an environmentally harmonizing plastic material, which hardly produces any bad effect on the ecological system. In recent years, from the viewpoint of environmental pollution, waste disposal and petroleum resources, synthetic plastics have been becoming serious social problems. Thus, attention has been paid to PHAs as environment-friendly green plastic materials. It has been strongly desired to put PHAs into practical use.

A PHA first discovered in microorganisms is a polyhydroxybutyrate (a PHB), which is a homopolymer made from 3-hydroxybutyric acid (abbreviated hereinafter to 3HB). The PHB is high in crystallinity, and high in crystallization degree to be hard and brittle, and further the PHB is rapidly thermally decomposed at a temperature (180° C.) around the melting point thereof. Accordingly, the PHB has problems that this resin is low in melt workability and a practical use scope thereof is very restrictive.

Thus, in order to lower the PHB in crystallization degree to be improved in brittleness, attempts have been made in which another 3-hydroxyalkanoic acid is introduced into the skeleton of the PHB. In one of the attempts, a copolymer polyester has been discovered which is made from 3HB and 3-hydroxyhexanoic acid (abbreviated hereinafter to 3HH) (this polyester P(3HB-co-3HH) will be abbreviated hereinafter to the PHBH). The PHBH, which contains, as a monomer unit, 3HH having a larger side chain structure (than PHB), is lower in crystallization degree than any PHB to have flexible and soft properties and improved in brittleness. Additionally the PHBH is low in melting point to be also expected to have improved melt workability. However, the following have been understood: the PHBH is very low in crystallization/solidification speed, and thus, even when cooled to room temperature after heated and melted, the PHBH has a soft property and is viscous for some time; and the PHBH has adhesiveness so that when molded, the PHBH is not immediately released from the mold. For the reason, in cases of putting the PHBH into practical use, some of the cases do not attain actual and continuous production of the PHBH. It has also become evident that working machines used to work existing commodity plastics high crystallization/solidification speed may not be usable for working the PHBH. In working into a film or sheet, a fiber, a foam, a molded product, or a nonwoven fabric, it is very important when a melt-worked polymer is cooled that the crystallization/solidification speed of this polymer is high since this high speed results in making the producing process of such articles continuous, followed by an improvement of the articles in productivity and a fall in costs thereof.

Thus, attempts have been made for making a PHBH high in crystallization/solidification speed. As an ordinary method therefor, a method of adding, to the PHBH, a nucleating agent has been attempted. According to, for example, Patent Literature 1, boron nitride is used as the nucleating agent for PHBH to produce a crystallization promoting effect. However, this is an expensive material, and further has no biodegradability. Consequently, a less expensive and more biodegradable nucleating agent has been investigated.

Patent Literatures 2 and 3 each disclose a technique of adding a PHB, which is higher in melting point than a PHBH and is further biodegradable, as a nucleating agent to the PHBH to make the resultant high in crystallization/solidification speed. According to these preceding literatures, as a method of blending the PHBH with the PHB, for example, the following has been attempted: a method of dissolving the PHBH and the PHB in a solvent such as hot chloroform, blending these solutions with each other, and then evaporating chloroform to precipitate polymers; a method of pulverizing the two polymers to be blended with each other while the polymers are cooled with dry ice; or blending these polymers in the state that only the PHBH is melted without melting the PHB, or blending these polymers by mixing dry powders of the polymers with each other. However, the method of dissolving the polymers in the solvent to be mixed with each other requires a very large quantity of the solvent for dissolving or crystalizing the PHBH, so as to become high in costs. As the method of blending the PHBH with the PHB, a method is also known in which these polymers are subjected to crystallization with methanol and the resultant mixed polymers are collected. Because of a difference in solubility between the polymer and the nucleating agent at the time of the crystallization, this method has, for example, a probability that the crystallization may not be performed in the state that the nucleating agent is uniformly dispersed. Thus, this method is not practical. In the method of pulverizing the polymers and subsequently blending the polymers with each other, or the method of mixing the dry polymer powders, it is difficult to blend the polymers uniformly with each other. It is therefore anticipated that the effect of the nucleating agent is lowered. As the respective particle diameters of the PHBH and the nucleating agent are smaller, these are more sufficiently blended with each other and further the number of nucleus-forming moieties becomes larger. Thus, a higher advantageous effect is expected. However, in the blending methods described above, the blending effect based on such fine particles is not expectable. Furthermore, in order to disperse the PHB uniformly in the PHBH, working at a temperature not lower than the melting point of the PHB is required. However, ordinary species of the PHB have a high melting point. Additionally, as described above, the species are thermally decomposed at a temperature around the melting point. Thus, when the PHB is dispersed in the PHBH, the PHB and the PHBH are deteriorated by heat, so that a fall in the molecular weight thereof, and other problems are not easily avoidable.

In order to solve these problems, a method has been invented in which a microorganism is caused to produce a PHBH, and a PHA, which is a nucleating agent, in a mixed state by controlling the culture of the microorganism. For example, Patent Literature 4 reports a method of changing a carbon source in the middle of the culture to cause a microorganism to produce a mixture of a PHBH, and a PHB or a PHBH having a low copolymerization proportion of a 3HH monomer. Non-Patent Literature 1 suggests that a culture of a microorganism using a specific plant oil and sodium valerate as carbon sources makes it possible to co-produce, in a cell of the microorganism, a mixture of a PHB, and a copolymer polyester made from 3HB and 3-hydroxyvaleric acid (abbreviated hereinafter to 3HV) (this polyester P(3HB-co-3HV) will be abbreviated hereinafter to the PHBV). These methods do not require independent production of a nucleating agent component such as a PHB to have a large advantage in terms of costs. However, in the method in Patent Literature 4, in which the carbon source is changed in the middle of the culture, two PHAs are non-continuously produced so that the control of the culture is very difficult. Furthermore, the method is low in productivity so that the polymer is not produced stably. Moreover, in the method in Non-Patent Literature 1, a target advantageous effect is obtained only when the specific plant oil is used. Furthermore, it is difficult to control a blend quantity ratio between the two PHAs. Thus, this method is impractical.

Additionally, as an example in which two PHAs are intracellularly co-produced, the following are reported. For example, Non-Patent Literature 2 reports that a wild-type 61-3 strain of the genus *Pseudomonas* has three genes encoding PHA synthases. Two of these three PHA synthases have, as their substrate, a medium-chain-length 3-hydroxy-alkanoic acid having a carbon chain length of 6 to 12, and one thereof has, as its substrate, only 3HB. Therefore, when this 61-3 strain is cultured in a culture medium containing a fatty acid such as octanoic acid or dodecanoic acid, a medium-chain-length PHA and a PHB are intracellularly co-produced. Non-Patent Literatures 3 and 4 each report that when a gene encoding a PHB synthase derived from a bacterium that may be of various types is introduced into a *Pseudomonas oleovorans* that synthesizes a medium-chain-length PHA, the medium-chain-length PHA and a PHB are intracellularly co-produced. Non-Patent Literature 5 reports that when a gene encoding a medium-chain-length PHA synthase derived from *Allochromatium vinosum* is introduced into *Ralstonia eutropha* that synthesizes a PHB, the PHB and a medium-chain-length PHA are intracellularly co-produced.

CITATION LIST

Patent Literatures

PTL 1: JP H06-157878 A
PTL 2: JP H08-510498 A
PTL 3: WO 2002/50156
PTL 4: JP 2004-250629 A

Non-Patent Literatures

NPLT 1: Wing-Hin Lee, Ching-Yee Loo, Christopher T Nomura, Kumar Sudesh, Bioresource Technology, vol. 99, pp. 6844-6851, (2008)
NPLT 2: Hiroini Matsusaki, Sumihide Manji, Kazunori Taguchi, Mikiya Kato, Toshiaki Fukui, Yosiharu Doi, Journal of Bacteriology; vol. 180, pp. 6459-6467, (1998)
NPLT 3: Arnulf Timm, David Byrom, Alexander Steinbuchel, Applied Microbiology and Biotechnology, vol. 33, pp. 296-301, (1990)
NPLT 4: Matthias Liebergesell, Frank Mayer, Alexander Steinbuchel, Applied Microbiology and Biotechnology, vol. 40, pp. 292-300, (1993)
NPLT 5: Kawalpreet K. Aneja, Richard D. Ashby, Daniel K. Y. Solaiman, Biotechnology Letters, vol. 31, pp. 1601-1612, (2009)

SUMMARY OF INVENTION

Technical Problem

An object of the present invention is to improve the crystallization speed of a PHA copolymer which is slowly crystallized to improve the melt workability of the PHA copolymer in working such as injection molding, film molding, blow molding, fiber spinning, extrusion foaming or bead foaming, thereby improving the resultant articles in productivity.

Solution to Problem

In order to solve the above-mentioned problems, the inventors have repeatedly researched to find out that when a microorganism is used which has both of a gene encoding a PHA synthase that synthesizes a copolymer PHA, such as a PHBH, as a main polymer, and a gene encoding a PHA synthase that synthesizes a higher-melting-point PHA serving as a nucleating agent to co-produce the two PHAs in the same cell of the microorganism, the resultant PHA copolymer-containing resin is remarkably improved in crystallization speed. Thus, the present invention has been achieved.

Accordingly, a first aspect of the present invention relates to a method for producing a PHA mixture, including the step of culturing a microorganism having both of a gene encoding a PHA synthase that synthesizes a copolymer PHA (A) and that is derived from the genus *Aeromonas*, and a gene encoding a PHA synthase that synthesizes a PHA (B) different in melting point from the copolymer PHA (A) by 10° C. or more to produce, in a cell of the microorganism, two or more PHAs different in melting point from one another by 10° C. or more simultaneously. The copolymer PHA (A) is preferably a copolymer containing, as monomer units, at least 3HB and 3HH. It is preferred that the resultant PHA mixture shows at least two endothermic peaks between 85° C. and 180° C. in a DSC curve of the mixture and, among these endothermic peaks, an endothermic peak at the highest temperature has a calorie of 0.2 to 20 J/g; or the resultant PHA mixture shows only one endothermic peak between 85° C. and 180° C. in a DSC curve of the mixture, and the endothermic calorie at temperatures higher than 160° C. is from 0.5 to 10 J/g.

A second aspect of the present invention relates to a microorganism including a gene encoding a PHA synthase that synthesizes a copolymer PHA (A) and that is derived from the genus *Aeromonas*, and a gene encoding a PHA synthase that synthesizes a PHA (B) different in melting point from the copolymer PHA (A) by 10° C. or more. The gene encoding the PHA synthase that synthesizes the copolymer PHA (A) and that is derived from the genus *Aeromonas* is preferably a gene encoding a protein having an amino acid sequence shown in SEQ ID NO: 1, or a gene encoding a protein having a sequence homology of 85% or more to the amino acid sequence and having a PHA synthase activity. The gene encoding the PHA synthase that synthesizes the PHA (B) is preferably a gene encoding a PHA synthase derived from a biological species different from the genus *Aeromonas*: is more preferably a gene encoding a PHA synthase derived from the genus *Cupriavidus*: and is even more preferably a gene encoding an amino acid sequence shown in SEQ ID NO: 4 derived from *Cupriavidus necator*, or a gene encoding a protein having a sequence homology of 85% or more to the amino acid sequence and having a PHA synthase activity.

Furthermore, the microorganism preferably belongs to the genus *Cupriavidus*, and is more preferably *Cupriavidus necator*. Moreover, the microorganism is preferably a microorganism which further has a gene encoding an (R)-specific enoyl-CoA hydratase, and the expression of the gene encoding the (R)-specific enoyl-CoA hydratase is enhanced; or a microorganism which has a phbA gene and/or a bktB gene, and the expression of the phbA gene is restrained, and/or the expression of the bktB gene is enhanced.

Advantageous Effects of Invention

The present invention makes it possible to remarkably improve the crystallization speed of a PHA copolymer which is slowly crystallized to improve the melt workability or working speed of the PHA copolymer in working such as injection molding, film molding, blow molding, fiber spinning, extrusion foaming or bead foaming.

BRIEF DESCRIPTION OF DRAWINGS

FIG. 1 shows a DSC curve obtained by measuring a PHA mixture obtained in Example 2.

FIG. 2 shows a DSC curve obtained by measuring a PHA mixture obtained in Example 5.

FIG. 3 shows a DSC curve obtained by measuring a PHA obtained in Comparative Example 1.

FIG. 4 shows a DSC curve obtained by measuring a PHA mixture obtained in Example 9.

FIG. 5 shows a DSC curve obtained by measuring the PHA mixture obtained in Example 9 after this mixture was annealed.

FIG. 6 shows a DSC curve obtained by measuring a PHA mixture obtained in Example 10.

FIG. 7 shows a DSC curve obtained by measuring the PHA mixture obtained in Example 10 after this mixture was annealed.

FIG. 8 shows a DSC curve obtained by measuring a PHA obtained in Comparative Example 2.

DESCRIPTION OF EMBODIMENTS

Hereinafter, the present invention will be described in more detail.

In the present invention, a microorganism is used which has both of a gene encoding a PHA synthase that synthesizes a copolymer PHA (A) and that is derived from the genus *Aeromonas*, and a gene encoding a PHA synthase that synthesizes a PHA (B) different in melting point from the copolymer PHA by 10° C. or more (hereinafter, this microorganism will be referred to as the "microorganism of the present invention").

In the microorganism of the present invention, the gene encoding a PHA synthase that synthesizes a copolymer PHA (A) and that is derived from the genus *Aeromonas* is not particularly limited as far as the gene is a gene encoding a PHA synthase which can synthesize a copolymer PHA and that is derived from the genus *Aeromonas*. The gene is preferably a gene encoding a PHA synthase which can synthesize a copolymer PHA containing, as monomer units, at least 3HB and 3HH, and is more preferably a gene encoding a PHA synthase which can synthesize a PHBH, which is a copolymer of 3HB and 3HH. Such a PHA synthase-encoding gene is, for example, preferably a PHA synthase-encoding gene derived from *Aeromonas caviae* or *Aeromonas hydrophila*, and is more preferably the PHA synthase-encoding gene derived from *Aeromonas caviae*. This PHA synthase-encoding gene, which is derived from *Aeromonas caviae*, may be a gene encoding a protein having an amino acid sequence shown in SEQ ID NO: 1, or a gene encoding a protein having a sequence homology of 85% or more, preferably 90% or more, more preferably 95% or more to the amino acid sequence and having a PHA synthase activity. A specific example of the gene encoding a protein having an amino acid sequence shown in SEQ ID NO: 1 is a gene shown in SEQ ID NO: 2. A specific example of the gene encoding a protein having a sequence homology of 85% or more to the amino acid sequence shown in SEQ ID NO: 1 and having a PHA synthase activity is a gene shown in SEQ ID NO: 3.

The microorganism of the present invention is characterized by having at least two genes encoding PHA synthases, that include not only the above-mentioned gene, which encodes a PHA synthase that synthesizes a copolymer PHA (A) and that is derived from the genus *Aeromonas*, but also a gene encoding a PHA synthase that synthesizes a PHA (B) different in melting point from the copolymer PHA (A) by 10° C. or more. The microorganism of the present invention may have a third gene encoding a PHA synthase besides the above-mentioned two genes, one of which encodes a PHA synthase that synthesizes a copolymer PHA (A) and that is derived from the genus *Aeromonas*, and the other of which encodes a PHA synthase that synthesizes a PHA (B). The microorganism of the present invention may also have, in a single cell thereof, a plurality of genes encoding a PHA synthase that synthesize a copolymer PHA (A) and that are derived from the genus *Aeromonas*, and/or genes encoding a PHA synthase that synthesize a PHA (B).

The copolymer PHA (A) and the PHA (B) are not particularly limited as far as the PHA (B) is different in melting point from the copolymer PHA (A) by 10° C. or more. Preferably, the PHA (B) is higher in melting point than the copolymer PHA (A). The melting point of the PHA (B) is preferably 165° C. or higher, more preferably 170° C. or higher. When the PHA (B) is higher in melting point than the copolymer PHA (A), the copolymer PHA (A) may be a main polymer and the PHA (B) may be a nucleating agent for the copolymer PHA (A). This PHA (B) may be a copolymer PHA, or a PHB, which is a homopolymer. When the PHA (B) is a copolymer PHA, the PHA (B) may be a PHBH, a PHBV, or a copolymer other than these polymers. The PHA (B) is preferably a polymer containing, as a polymer unit, 3HB in a proportion of 95% by mole or more; more preferably a polymer containing 3HB in a proportion of 97% by mole or more; even more preferably a polymer containing 3HB in a proportion of 99% by mole or more. The PHA (B) is especially preferably a PHB, which is a homopolymer.

The above-mentioned gene which encodes a PHA synthase that can synthesize a PHA (B) is not particularly limited. For example, the gene encoding a PHA synthase that can synthesize a high-melting-point copolymer PHA as the PHA (B) may be a gene encoding a single amino acid substitute (such as PhaC$_{AC}$A505W) of a PHA synthase derived from *Aeromonas caviae*. The PhaC$_{AC}$A505W makes it possible to synthesize a copolymer PHA containing 3HB in a proportion of 99% by mole or more. In the meantime, there are many genes each encoding a PHA synthase that synthesizes a PHB (see, for example, Biopolymers Volume 3a, Polyesters I, edited by Y. DOI and A. STEINBUCHEL, 2002). Any one of these genes is usable. Specific examples of the genes include genes each encoding a PHA synthase derived from the genus *Acinetobacter, Aeromonas, Alcaligenes, Allochromatium, Azorhizobium, Azotobacter, Bacillus, Burkholderia, Caulobacter, Chromobacterium, Comamonas, Cupriavidus, Ectothiorhodospira, Klebsiella, Methylobacterium, Paracoccus, Pseudomonas, Ralstonia, Rhizobium, Rhodobacter, Rhodococcus, Rhodospirillum, Rickettsia, Sinorhizobium, Sphingomonas, Synechocystis, Thiococcus, Thiocystis, Vibrio, Wautersia,* or *Zoogloea*; and genes each encoding a variant of the PHA synthase. In the present invention, the gene encoding a PHA synthase that synthesizes a PHA (B) is preferably a gene encoding a PHA synthase derived from a biological species different from the genus *Aeromonas,* more preferably a gene encoding a PHA synthase derived from the genus *Cupriavidus,* even more preferably a gene encoding a PHA synthase derived from *Cupriavidus necator,* especially preferably a gene encoding a protein having an amino acid sequence shown in SEQ ID NO: 4, or a gene encoding a protein having a sequence homology of 85% or more, preferably 90% or more, more preferably 95% or more to the amino acid sequence described above and having a PHA synthase activity. The gene encoding a protein having an amino acid sequence shown in SEQ ID NO: 4 is, for example, a gene derived from *Cupriavidus necator* and shown in SEQ ID NO: 5.

In the present invention, a microorganism that is to be a host for having the two genes encoding the above-mentioned PHA synthases is not particularly limited. Examples thereof include microorganisms belonging to the genera *Acinetobacter, Aeromonas, Alcaligenes, Allochromatium, Azorhizobium, Azotobacter, Bacillus, Burkholderia, Candida, Caulobacter, Chromobacterium, Comamonas, Cupriavidus, Ectothiorhodospira, Escherichia, Klebsiella, Methylobacterium, Nocardia, Paracoccus, Pseudomonas, Ralstonia, Rhizobium, Rhodobacter, Rhodococcus, Rhodospirillum, Rickettsia, Saccharomyces, Sinorhizobium, Sphingomonas, Synechocystis, Thiococcus, Thiocystis, Vibrio, Wautersia,* and *Zoogloea.* Among these microorganisms, microorganisms belonging to, for example, the genera *Aeromonas, Alcaligenes, Cupriavidus, Escherichia, Pseudomonas,* and *Ralstonia* are more preferred. Microorganisms belonging to the genera *Cupriavidus, Escherichia,* and *Ralstonia* are even more preferred. Microorganisms belonging to the genus *Cupriavidus* are even more preferred. *Cupriavidus necator* is particularly preferred.

No particular limitation is given to a method for causing the microorganism of the present invention to have, in the same cell thereof, at least two genes encoding PHA synthases, which are a gene encoding a PHA synthase that synthesizes a copolymer PHA (A) and that is derived from the genus *Aeromonas,* and a gene encoding a PHA synthase that synthesizes a PHA (B). However, such a microorganism has not been discovered in the natural world up to the present. Thus, it is necessary to use, for example, a gene recombination technique to introduce, into a microorganism which is to be a host, either the gene encoding a PHA synthase that synthesizes a copolymer PHA (A) and that is derived from the genus *Aeromonas* or the gene encoding a PHA synthase that synthesizes a PHA (B), or both of the genes. For example, it is allowable to introduce the gene encoding a PHA synthase that synthesizes a PHA (B) to a microorganism belonging to the genus *Aeromonas* and originally having the gene encoding a PHA synthase that synthesizes a copolymer PHA (A); or introduce the gene encoding a PHA synthase that synthesizes a copolymer PHA (A) and that is derived from the genus *Aeromonas* into a microorganism having the gene encoding a PHA synthase that synthesizes a PHA (B) such as a PHB (this microorganism is, for example, *Cupriavidus necator*). It is also allowable to introduce, into any microorganism that is to be a host, both of the gene encoding a PHA synthase that synthesizes a copolymer PHA (A) and that is derived from the genus *Aeromonas,* and the gene encoding a PHA synthase that synthesizes a PHA (B). From the viewpoint of expression levels that will be described later, and easy adjustment of the ratio therebetween, it is preferred to introduce, into any microorganism that is to be a host, both of the gene encoding a PHA synthase that synthesizes a copolymer PHA (A) and that is derived from the genus *Aeromonas,* and the gene encoding a PHA synthase that synthesizes a PHA (B). It is particularly preferred to introduce, into a microorganism belonging to the genus *Cupriavidus,* both of the gene encoding a PHA synthase that synthesizes a copolymer PHA (A) and that is derived from the genus *Aeromonas,* and the gene encoding a PHA synthase that synthesizes a PHB and that is derived from a microorganism belonging to the genus *Cupriavidus.* In this case, a gene encoding a PHA synthase which the microorganism belonging to the genus *Cupriavidus* originally has may be present as it is, or may be disrupted or deleted. It is preferred that this gene is disrupted or deleted in an unexpressed state.

The method for introducing the gene encoding a PHA synthase is not particularly limited. Any method may be selected from the following methods, or a combination of any two or more of the following methods may be used: a method of inserting the gene immediately onto a chromosome of a host, or substituting the gene onto the chromosome; a method of introducing the gene onto a megaplasmid which a host has; and a method of arranging the gene on a vector such as a plasmid, phage or phagemid to be introduced thereinto. However, any plasmid may drop out from a cell while the cell is cultured; thus, it is preferred to insert or substitute, onto a chromosome of a host, either the gene encoding a PHA synthase that synthesizes a copolymer PHA (A) and that is derived from the genus *Aeromonas* or the gene encoding a PHA synthase that synthesizes a PHA (B), or both of the genes. The method for each of the introduction, the insertion, the substitution, and the arrangement may be any known method. For example, a homologous recombination method is usable, for example, for inserting the above-mentioned PHA synthase-encoding gene onto a chromosome of a microorganism which is to be a host, or substituting the PHA synthase-encoding gene onto the chromosome.

The microorganism of the present invention preferably has the following located upstream of each of the gene encoding a PHA synthase that synthesizes a copolymer PHA (A) and that is derived from the genus *Aeromonas,* and the gene encoding a PHA synthase that synthesizes a PHA (B): an "expression regulatory sequence" related to the expression of the gene. The "expression regulatory sequence" referred to herein may be specifically a DNA sequence positioned upstream of a start codon of the gene encoding the PHA synthase to control the transcription quantity of the gene, or a DNA sequence for adjusting the translational level of a messenger RNA transcribed from this gene (for example, an SD sequence (Shine Dalgarno sequence); or a DNA sequence including the two DNA sequences. As the expression regulatory sequence linked upstream of each of the gene encoding a PHA synthase that synthesizes a copolymer PHA (A) and that is derived from the genus *Aeromonas,* and the gene encoding a PHA synthase that synthesizes a PHA (B), the following is usable: an expression regulatory sequence which a host originally has; any expression regulatory sequence present in the natural world; or an artificially constructed or modified expression regulatory sequence. When one operon includes the gene encoding a PHA synthase that synthesizes a copolymer PHA (A) and that is derived from the genus *Aeromonas*, and the gene encoding a PHA synthase that synthesizes a PHA (B), these genes may have a common expression regulatory sequence.

The expression regulatory sequence used in the microorganism of the present invention is not particularly limited. As described above, an expression regulatory sequence which a host originally has may be used. Alternatively, it is allowable that when the PHA synthase-encoding-gene is introduced into the microorganism, an expression regulatory sequence positioned upstream thereof is together introduced as it is; or it is allowable that for either or both of the genes encoding the PHA synthases to be introduced, one or two preferred expression regulatory sequences are selected, the selected sequence(s) is/are linked to the gene(s), and then the resultant(s) is/are introduced into a host.

From the viewpoint of ease of the production of the microorganism, and the expression level control that will be detailed later, it is preferred to use, as the expression regulatory sequence for the gene encoding a PHA synthase that synthesizes a copolymer PHA (A) and that is derived from the genus *Aeromonas*, an expression regulatory sequence for a gene encoding a PHA synthase which a host originally has; select, as the expression regulatory sequence for the gene encoding a PHA synthase that synthesizes a PHA (B), a sequence that can optimize the intracellular presence quantity of the PHA synthase in accordance with a target expression level or translation level, and others; and then link the selected expression regulatory sequence with the gene encoding a PHA synthase that synthesizes a PHA (B) to introduce this sequence-linked gene into the host, or insert the sequence into an upstream thereof.

The expression regulatory sequence for the gene encoding a PHA synthase that synthesizes a PHA (B) is not particularly limited, and may be any naturally-derived expression regulatory sequence, or any variant thereof. Specifically, the promoter for regulating the transcriptional activity of the gene may be a lac promoter shown in SEQ ID NO: 6, which is a promoter derived from *E. coli*, a trp promoter shown in SEQ ID NO: 7, a lacUV5 promoter shown in SEQ ID NO: 8, which is a variant of any one of these promoters, a lacN15 promoter shown in SEQ ID NO: 56, a lacN16 promoter shown in SEQ ID NO: 57, a lacN17 promoter shown in SEQ ID NO: 58, a lacN19 promoter shown in SEQ ID NO: 59, a lacN20 promoter shown in SEQ ID NO: 60, a lacN21 promoter shown in SEQ ID NO: 61, a tacI promoter shown in SEQ ID NO: 9, a tacII promoter shown in SEQ ID NO: 10, a tic promoter shown in SEQ ID NO: 11, or a trc promoter shown in SEQ ID NO: 12; and may further be a REP promoter shown in SEQ ID NO: 13, which is a promoter for a phaCAB operon derived from *Cupriavidus necator*, a REPN17 promoter shown in SEQ ID NO: 14, which is a variant of the REP promoter, or a phaP1 promoter shown in SEQ ID NO: 15, which is a promoter for a phaP1 gene encoding phasin derived from *Cupriavidus necator*. These promoters are each usable as an expression regulatory sequence by linking to a sequence REP-SD shown in SEQ ID NO: 16, which is an SD sequence of phaC1 gene derived from *Cupriavidus necator*, a sequence REP-SDM shown in SEQ ID NO: 17, which is a variant of the REP-SD, any other known SD sequences, or any expression regulatory sequences equivalent thereto. Moreover, any other known expression regulatory sequence is also usable, examples thereof including an expression regulatory sequence PJ4a shown in SEQ ID NO: 18, which is made of the promoter for the operon including four genes of A1067, A1068, A1069 and phaJ4a derived from *Cupriavidus necator* and the SD sequence of A1067, and an expression regulatory sequence Pac shown in SEQ ID NO: 19, which is made of the promoter for phaPCJ operon derived from *Aeromonas caviae*, and the SD sequence of phaP. Furthermore, usable is also an expression regulatory sequence obtained by modifying any one of these expression regulatory sequences by deletion, substitution or insertion of a base.

In the present invention, an appropriate selection of the expression regulatory sequence(s) to be used makes it possible to adjust the intracellular presence quantity of each of the PHA synthases to control the respective production quantities of the copolymer PHA (A) and the PHA (B) different in melting point from the PHA (A), and the ratio therebetween. In order to control the ratio between the two produced PHAs different in melting point from each other, it is preferred to adjust the ratio between the respective presence quantities of the individual intracellular PHA synthases, or the ratio between the respective expression levels of the genes encoding the individual PHA synthases. It is preferred on the basis of this viewpoint to select a combination of an expression regulatory sequence of the gene encoding a PHA synthase that synthesizes a copolymer PHA (A) and that is derived from the genus *Aeromonas* with an expression regulatory sequence for the gene encoding a PHA synthase that synthesizes a PHA (B). Such a combination of the expression regulatory sequences is selectable considering, for example, the intensity of one or more promoters to be used, the enzyme activity of the target PHA synthases, the metabolic system of the host, and others.

For example, when the copolymer PHA (A) has 3HH as a monomer unit and the copolymerization proportion of the 3HH monomer in the copolymer is relatively high, specifically, when the copolymer PHA (A) is a copolymer containing 8% by mole or more of the 3HH monomer unit, it is preferred to control the content of the PHA (B) in a PHA mixture to be produced in the range of 0.1 to 20% by weight of the total amount of the copolymer PHA (A) and the PHA (B) in this mixture. A reason therefor will be described later. The microorganism for obtaining such a PHA mixture is not particularly limited. It is preferred to use, as a host, *Cupriavidus necator* H16 strain in which the gene encoding a PHA synthase that synthesizes a copolymer PHA (A) and that is derived from the genus *Aeromonas* is inserted or substituted onto a chromosome. In this case, the expression regulatory sequence for the gene encoding a PHA synthase that synthesizes a copolymer PHA (A) and that is derived from the genus *Aeromonas* is preferably an expression regulatory sequence made of REP and REP-SD which the *Cupriavidus necator* H16 strain originally has. In this case, the expression regulatory sequence for the gene encoding a PHA synthase that synthesizes a PHA (B) is preferably an expression regulatory sequence made of a combination of the following with either REP-SD or REP-SDM, which is a variant of REP-SD, as an SD sequence: any one of the above-mentioned lac promoter, a variant obtained by introducing a mutation into the spacer sequence of lac promoter (the variant being, for example, a lacN15 promoter, a lacN16 promoter, a lacN17 promoter, a lacN19 promoter, a lacN20 promoter or a lacN21 promoter), and a REP promoter. Alternatively, the expression regulatory sequence is preferably the above-mentioned PJ4a, or an expression regulatory sequence capable of adjusting the intracellular presence quantity of a PHA synthase to the same degree as attained by these expression regulatory sequences. The expression regulatory sequence is more preferably an expression regulatory sequence including DNA sequences represented by SEQ ID NOs: 6 and 16, an expression regulatory sequence including DNA sequences represented by SEQ ID NOs: 6 and 17, an expression regulatory sequence including DNA sequences represented by SEQ ID NOs: 56 and 17, an expression regulatory sequence including DNA sequences represented by SEQ ID NOs: 59 and 17, an expression regulatory sequence shown in SEQ ID NO: 18, or any expression regulatory sequence equivalent in expression intensity to these expression regulatory sequences. In the same manner, any different combination equivalent in the following ratio to the above-mentioned preferred combinations is also preferably adoptable: the ratio between the expression intensity of the expression regulatory sequence for the gene encoding a PHA synthase that synthesizes a copolymer PHA (A) and that is derived from the genus *Aeromonas*, and that of the expression regulatory sequence for the gene encoding a PHA synthase that synthesizes a PHA (B).

Moreover, in order to produce, as the copolymer PHA (A), the copolymer containing 8% by mole or more of the 3HH monomer unit, it is preferred to use, as the microorganism to be used, a microorganism not only which has genes encoding the above-mentioned two PHA synthases but also which makes a device of heightening the copolymerization proportion of the 3HH monomer in the resultant copolymer PHA (A). The device may be a method of enhancing the expression of a gene encoding an (R)-specific enoyl-CoA hydratase; or a method of restraining a phbA gene among genes encoding an enzyme having β-ketothiolase activity; and/or a method of enhancing the expression of a bktB gene. The method of enhancing the expression of a gene encoding an (R)-specific enoyl-CoA hydratase is not particularly limited. For example, when *Cupriavidus necator* is used as a host, examples of this method include a method of inserting the following upstream of the gene encoding an (R)-specific enoyl-CoA hydratase present on a chromosome (the gene being, for example, a gene phaJ4a or phaJ4b): an expression regulatory sequence made of a REP promoter and REP-SD; an expression regulatory sequence made of a REP promoter and REP-SDM; an expression regulatory sequence made of a PEPN17 promoter, which is a variant of the REP promoter, and REP-SD; an expression regulatory sequence made of the same PEPN17 promoter and REP-SDM; or an expression regulatory sequence made of a known promoter derived from *E. coli* (for example, a trp promoter), and any SD sequence including, as an example, REP-SD or REP-SDM. In the meantime, the method of restraining the expression of a phbA gene, and/or the method of enhancing the expression of a bktB gene may be, for example, a method described in WO 2009/145164. Of course, it is allowable to heighten the copolymerization proportion of the 3HH monomer in the resultant copolymer PHA (A) without using these methods, for example, by changing culturing conditions for the microorganism, such as aeration stirring conditions and a carbon source.

In the meantime, when the copolymer PHA (A) has 3HH as a monomer unit and the copolymerization proportion of the 3HH monomer in this copolymer is not very high, specifically, when the copolymer PHA (A) is a copolymer containing the 3HH monomer unit in a proportion of 3% by mole or more and less than 8% by mole, it is preferred to control the content of the PHA (B) in a PHA mixture to be produced in the range of 3% by weight or more of the total amount of the copolymer PHA (A) and the PHA (B) in this mixture. A reason therefor will be described later. In general, when the copolymerization proportion of the 3HH monomer in the copolymer PHA (A) is less than 8% by mole, it is preferred that the content of the PHA (B) is to some extent high. It is therefore preferred to use an expression regulatory sequence which is to some extent high in expression intensity as the expression regulatory sequence linked to the gene encoding a PHA synthase that synthesizes a PHA (B). The microorganism for obtaining such a PHA mixture is not particularly limited. It is preferred to use, as a host, *Cupriavidus necator* H16 strain in which the gene encoding a PHA synthase that synthesizes a copolymer PHA (A) and that is derived from the genus *Aeromonas* is inserted or substituted onto a chromosome. In this case, the expression regulatory sequence for the gene encoding a PHA synthase that synthesizes a copolymer PHA (A) and that is derived from the genus *Aeromonas* is preferably an expression regulatory sequence made of REP and REP-SD which the *Cupriavidus necator* H16 strain originally has. Moreover, the expression regulatory sequence for the gene encoding a PHA synthase that synthesizes a PHA (B) is preferably the above-mentioned expression regulatory sequence made of REP and REP-SD, an expression regulatory sequence made of a lacUV5 promoter and REP-SD, an expression regulatory sequence made of a lac promoter and REP-SD, an expression regulatory sequence made of a tacI promoter and REP-SD, or any expression regulatory sequence equivalent in expression activity to these expression regulatory sequences; and is more preferably an expression regulatory sequence including DNA sequences represented by SEQ ID NOs: 13 and 16, an expression regulatory sequence including DNA sequences represented by SEQ ID NOs: 8 and 16, an expression regulatory sequence including DNA sequences represented by SEQ ID NOs: 6 and 16, an expression regulatory sequence including DNA sequences represented by SEQ ID NOs: 9 and 16, or any expression regulatory sequence equivalent in expression intensity to these expression regulatory sequences.

In the present invention, the microorganism of the present invention is cultured to produce, in cells thereof, two PHAs different in melting point from each other by 10° C. or more preferably at the same time, and then the PHAs are collected from the microbial cells. In this way, a PHA mixture including the two PHAs can be produced.

A carbon source at the time of the culture may be any carbon source as far as the PHA-producing microorganism of the present invention is capable of assimilating the carbon source. The carbon source is preferably a saccharide such as glucose, fructose or sucrose; an oil and fat such as palm oil, palm kernel oil, corn oil, coconut oil, olive oil, soybean oil, rapeseed oil or Jatropha oil, or a fractional oil thereof or a purified byproduct thereof; a fatty acid such as lauric acid, oleic acid, stearic acid, palmitic acid or myristic acid, or a derivative thereof. The carbon source is more preferably a plant oil and fat such as palm oil or palm kernel oil; or palm olein, palm double olein or palm kernel olein, which is a low-melting-point fraction obtained by fractionating palm oil or palm kernel oil; and a purified byproduct of an oil and fat, such as a PFAD (palm fatty acid distillate), a PKFAD (palm kernel fatty acid distillate) or a fatty acid distilled product of rapeseed oil, especially from the viewpoint of avoiding competition with food.

It is preferred in the production of the PHAs in the present invention to use a medium containing the carbon source, a nitrogen source, which is a nutrient source other than the carbon source, an inorganic salt, and any other organic nutrient source to culture the microorganism. Examples of the nitrogen source include ammonia, urea, and ammonium salts such as ammonium chloride, ammonium sulfate and ammonium phosphate, peptone, a meat extract, and a yeast extract. Examples of the inorganic salt include potassium dihydrogenphosphate, disodium hydrogenphosphate, magnesium phosphate, magnesium sulfate, and sodium chloride. Examples of the other organic nutrient source include amino acids such as glycine, alanine, serine, threonine and proline, and vitamins such as vitamins B1, B12 and C.

The culturing temperature, the culturing period, the pH at the time of the culturing, the medium, and other conditions may be culturing conditions as used ordinarily for the used microorganism.

In the present invention, the method for collecting the PHA mixture from the microbial cells is not particularly limited and may be, for example, a method as described hereinafter. After the end of the culturing, from the culture liquid, the microbial cell is separated by, for example, a centrifugal separator, and the microbial cell is washed with, for example, distilled water and methanol and then dried. From this dried microbial cell, an organic solvent such as chloroform is used to extract the PHA mixture. From this organic solvent solution containing the PHA mixture, any insoluble matter derived from the microbial cells is removed by, for example, filtration. A poor solvent such as methanol or hexane is added to the resultant filtrate to precipitate the PHA mixture. Furthermore, the supernatant is removed by filtration or centrifugation, and the remnant is dried to collect the PHA mixture.

The PHA mixture produced by the present invention includes at least two PHAs different in melting point from one another by 10° C. or more. It is preferred that, of the two, a PHA lower in melting point is a copolymer PHA (A) synthesized by the PHA synthase derived from the genus *Aeromonas*, and a PHA higher in melting point is a PHA (B) synthesized by the other PHA synthase. It is more preferred that the PHA (A) lower in melting point is a main polymer and the PHA (B) higher in melting point is a nucleating agent therefor. The copolymer PHA (A) is preferably a copolymer containing, as monomer units, 3HH and 3HB. The PHA (B) may be a copolymer PHA, or a PHB, which is a homopolymer. When the PHA (B) is a copolymer PHA, the copolymer contains, as a polymer unit, 3HB preferably in a proportion of 95% by mole or more, more preferably in a proportion of 97% by mole or more, even more preferably in a proportion of 99% by mole or more. The PHA (B) is especially preferably a PHB. The melting point of the PHA (B) is preferably 165° C. or higher, more preferably 170° C. or higher.

The matter that in the present invention, a mixture of two or more PHAs different in melting point from one another has been obtained can be checked by for example, a precipitation method as described in Patent Literature 3 using chloroform, or differential scanning calorimetry (DSC) that will be detailed later. However, the checking method is not limited to these methods. The crystallization state of any PHA may be varied in accordance with a thermal hysteresis based on a purification step or working step therefor, the temperature when the PHA is stored, and/or the passage of the storing period. Thus, when the matter is evaluated by DSC, it is preferred, from the viewpoint of minimizing the effects of these factors, to measure any measuring target rapidly in the state that the target is not yet worked.

When the copolymer PHA (A) is a copolymer containing 8% by mole or more of 3HH monomer units, the melting point thereof is about 130° C. or lower. Thus, the difference between this melting point and the melting point of the PHA (B), which is another PHA, is large so that evaluation based on the above-mentioned DSC becomes easy. In general, any PHA shows, in a DSC curve thereof, an endothermic peak derived from the melting point between 85° C. and 180° C. When the copolymer PHA (A) is a copolymer containing 8% by mole or more of 3HH monomer units and the PHA (B) is a PHB, the copolymer PHA (A) and the PHA (B) included in the PHA mixture show two endothermic peaks clearly different from each other between 85° C. and 180° C. in many cases, as shown typically in, for example, FIG. 2. However, when the content of a higher-melting-point PHA of the two PHAs is very small, an endothermic peak derived from this PHA may not be clearly identified.

When the copolymer PHA (A) is a copolymer containing 8% by mole or more of 3HH monomer units, the lower limit of the amount of the PHA (B) to the total amount of the copolymer PHA (A) and the PHA (B) in the PHA mixture is preferably 0.1% by weight or more, more preferably 0.5% by weight or more, even more preferably 1% by weight or more, especially preferably 1.2% by weight or more, most especially preferably 2% by weight or more. The upper limit of the amount of the PHA (B) is preferably 20% by weight or less, more preferably 15% by weight or less, even more preferably 12% by weight or less, especially preferably 9% by weight or less, most especially preferably 7% by weight or less. If the ratio of the PHA (B) is too small, the PHA (B) cannot have an effect as a nucleating agent. If the ratio of the PHA (B) is too large, the polymer may be lowered in ductility. The PHA mixture including the PHA (B) in a ratio in the above-mentioned preferred range can be identified by the following matter in a DSC curve of the mixture: about, among endothermic peaks in this curve, an endothermic peak at the highest temperature, the lower limit value of the calorie thereof is about 0.2 J/g or more, more preferably 0.5 J/g or more, even more preferably 1 J/g or more, especially preferably 1.5 J/g or more, most especially preferably 2 J/g or more; and the upper limit value of the calorie is about 20 J/g or less, more preferably 18 J/g or less, even more preferably 15 J/g or less, especially preferably 12 J/g or less, most especially preferably 8 J/g or less.

In the meantime, when the copolymer PHA (A) is a copolymer containing 3HH monomer units only in a proportion less than 8% by mole, the melting point thereof is relatively high. Thus, the difference between this melting point and the melting point of the PHA (B), which is another PHA, becomes small so that in a DSC curve of the mixture, endothermic peaks derived from the melting points may overlap with each other so that as shown typically in FIG. 4, only an apparently single endothermic peak may be shown between 85° C. and 180° C. In this case also, the matter that two PHAs different in melting point from each other have been produced can be determined by whether or not there is an endothermic portion at a temperature point higher than 160° C. When there is only a copolymer PHA (A) in which the content of 3HH monomer units is 3% by mole or more and less than 8% by mole, an endothermic peak in a DSC curve thereof ends at a temperature point lower than 160° C., as shown in FIG. 8. However, when this copolymer PHA (A) is present in the form of a mixture with a high-melting point PHA (B) such as a PHB, an endothermic peak in a DSC curve thereof comes to end at a temperature point higher than 160° C. since the melting point of the PHB is 165° C. or higher (FIGS. 4 and 6). Moreover, in such a way, the following case can also be identified: the case of a mixture in which the content of 3HH monomer units in a copolymer PHA (A) is 8% by mole or more but the content of a PHA (B) therein is very small so that an endothermic peak derived from the PHA (B) is unclear.

When a PHA mixture shows, in a DSC curve thereof, only apparently single endothermic peak between 85° C. and 180° C., a preferred content of the PHA (B) can be presumed from the area of an endothermic peak (endothermic calorie) at any temperature point higher than 160° C. In the present invention, when the PHA mixture in the present invention shows only a single endothermic peak in a DSC curve thereof, the lower limit value of the endothermic calorie at any temperature point higher than 160° C. is preferably 0.3 J/g or more, more preferably 0.4 J/g or more, even more preferably 0.5 J/g or more, even more preferably 1.5 J/g or more, especially preferably 3 J/g or more. The upper limit value of the endothermic calorie is preferably 15 J/g or less, more preferably 13 J/g or less, even more preferably 12 J/g or less, even more preferably 10 J/g or less, especially preferably 8 J/g or less.

When the copolymer PHA (A) is a copolymer containing 3HH monomer units in a proportion of 3% by mole or more and less than 8% by mole, the PHA (B) is preferably contained in a proportion of 3% by weight or more of the total of the copolymer PHA (A) and the PHA (B) in the PHA mixture, more preferably contained in a proportion of 5% by weight or more thereof, even more preferably contained in a proportion of 10% by weight or more thereof, especially preferably contained in a proportion of 12% by weight or more. If the proportion of the PHA (B) is too small, the PHA (B) cannot have an effect as a nucleating agent. When the copolymer PHA (A) is a copolymer containing 3HH monomer units in a proportion of 3% by mole or more and less than 8% by mole, the upper limit of the content of the PHA (B) is not particularly limited. Even when the content is considerably large, the PHA (B) does not largely affect physical properties of the polymer. The content is usually 50% by weight or less, preferably 40% by weight or less, more preferably 30% by weight or less. Furthermore, under specific forming conditions in, for example, the case of forming the mixture into a sheet form, the content is especially preferably 20% by weight or less in some cases.

The content of the PHA (B) in the PHA mixture can be presumed with higher precision by annealing the resultant PHA mixture, and then applying DSC thereto. Even when the PHA mixture particularly shows only an apparently single endothermic peak between 85° C. and 180° C. in a DSC thereof which is obtained without annealing the mixture, the application of DSC to the mixture after the mixture is annealed at 160° C. for 30 minutes causes the mixture to come to show two clear peaks at temperature points on both sides of about 160° C., as shown typically in FIG. 5. A higher-melting-point endothermic peak, of the two peaks, is an endothermic peak derived from the PHA (B). From the value of the calorie thereof, the ratio of the PHA (B) in the PHA mixture can be presumed.

When the copolymer PHA (A) is, for example, a copolymer containing 3HH monomer units in a proportion of 8% by mole or more, the lower limit value of the calorie of the higher-melting-point endothermic peak caused to emerge by the annealing is preferably 1.0 J/g or more, more preferably 1.5 J/g or more, even more preferably 2 J/g or more, especially preferably 2.5 J/g or more. The upper limit value of the calorie is preferably 13 J/g or less, more preferably 10 J/g or less, even more preferably 9 J/g or less, especially preferably 7 J/g or less. In the meantime, when the copolymer PHA (A) is a copolymer containing 3HH monomer units in a proportion of 3% by mole or ore and less than 8% by mole, the lower limit value of the calorie of the higher-melting-point endothermic peak caused to emerge by the annealing is preferably 2 J/g or more, more preferably 3 J/g or more, even more preferably 4 J/g or more, especially preferably 8 J/g or more. The lower limit value of the calorie is preferably 40 J/g or less, more preferably 37 J/g or less, even more preferably 35 J/g or less, especially preferably 30 J/g or less.

The molecular weight of any PHA produced in the present invention is not particularly limited. About each of the copolymer PHA (A) and the PHA (B), the weight-average molecular weight is preferably from 300,000 to 3,000,000, more preferably from 400,000 to 2,500,000, even more preferably from 500,000 to 2,000,000 for many usages from the viewpoint of melt workability. If the weight-average molecular weight of each of the PHAs is less than 300,000, the resultant mixture may be insufficient in mechanical properties such as strength. If the weight-average molecular weight is more than 3,000,000, the mixture may be poor in formability. However, depending on the usage thereof, the weight-average molecular weight is preferably from about 100,000 to 200,000 in some cases.

The PHA mixture produced by the present invention is a mixture improved in crystallization speed. The mixture may contain other additives, such as an antioxidant, an ultraviolet absorbent, colorants such as a dye and a pigment, a plasticizer, a lubricant, an inorganic filler, an antistatic agent, an anti-mold agent, an antibacterial agent, a foaming agent, and a flame retardant, as needed. The mixture may contain any other nucleating agent.

A resin composition obtained as described above can be formed/worked to be produced into a formed article. The method for the forming/working may be a method known in the prior art, such as injection molding, film molding, blow molding, fiber spinning, extrusion foaming, or bead foaming. The PHA mixture obtained by the production method of the present invention is not only a mixture improved in crystallization speed, but also a mixture in which a copolymer PHA, which is a main polymer, and a high-melting point PHA, which is to be a nucleating agent, are dispersed in each other at a molecular level. Thus, when this case is compared with the case of producing a copolymer PHA, and a high-melting-point PHA, which is to be a nucleating agent, separately and then blending the PHAs with each other, the nucleating agent in the former case can be finely dispersed in the main polymer by a simpler method, and further the mixture can be formed/worked at a lower temperature, for example, a temperature of 170° C. or lower.

The formed article is usable for, for example, various containers, packaging members, films for agriculture and horticulture, and medical materials.

EXAMPLES

Hereinafter, the present invention will be more specifically described by demonstrating working examples thereof. However, the invention is never limited to these examples. The following were used about the breeding of any bacterial strain, the monomer composition analysis of any PHA, analysis of the blend ratio between PHAs in any PHA mixture, crystallization evaluation, and a method for solidification-period-measurement.

Breeding of Bacterial Strain:

In the examples, any genetic manipulation can be attained by a method described in Molecular Cloning (Cold Spring Harbor Laboratory Press, 1989). Any enzyme, any cloning host and any other that are used in the genetic manipulation are commercially available from suppliers in the market, and are usable in accordance with their manual. The enzyme used in the examples is not particularly limited as far as the enzyme is usable in genetic manipulation.

Monomer Composition Analysis of PHA:

The monomer composition analysis of any resultant PHA was measured by gas chromatography: To about 20 mg of the resultant PHA or a mixture of the resultant PHAs were added 2 mL of a sulfuric-acid/methanol mixed liquid (15/85) and 2 mL of chloroform, and the system was air-tightly sealed. The system was heated at 100° C. for 140 minutes to subject the reactant to methyl esterification. After the system was cooled, 1.5 g of sodium hydrogencarbonate was added slowly to the reaction system to neutralize this system. The system was allowed to stand still until the generation of carbon dioxide was stopped. Thereto was added 4 mL of diisopropyl ether, and then the entire components were sufficiently mixed with one another, and then centrifuged. The composition of a methyl ester of 3HB and a methyl ester of 3HH in the supernatant was analyzed by capillary gas chromatography to calculate the proportion of the 3HH monomer. For the gas chromatography, the following were used: GC-17A manufactured by Shimadzu Corp.; and NEUTRA BOND-1 (column length: 25 m; column inside diameter: 0.25 mm; and liquid membrane thickness: 0.4 µm) manufactured by GL Sciences Inc. as a capillary column. As a carrier gas, He was used. The inlet pressure of the column was set to 100 kPa, and the volume of a poured sample was set to 1 µL. About temperature conditions, the temperature was raised from a starting temperature of 100° C. to 200° C. at a rate of 8° C./minute, and further the temperature was raised from 200° C. to 290° C. at a rate of 30° C./minute.

Analysis of Blend Ratio between PHAs in PHA Mixture:

About PHAs obtained by culturing followed by purification, the blend ratio between the PHAs was estimated by a method described below, using a differential scanning calorimeter (DSC 220, manufactured by SII NanoTechnology Inc.).

In a DSC thereof, the temperature of the PHAs, the weight of which was from 2 to 5 mg, was raised from 5° C. to 190° C. at a rate of 10° C./minute to give a DSC curve.

<Case where Two or more Clear Peaks are Observed between 85° C. and 180° C. in the Resultant DSC Curve>

In the DSC curve, about a main lower-temperature point endothermic peak (when three or more peaks between 85° C. and 180° C. are observed, this main peak denotes a maximum peak, among the observed peaks from which the highest-temperature point peak is excluded), the melting point shown by this main lower-temperature point endothermic peak is represented by Tm1. The melting point shown by the highest-temperature endothermic point peak is represented by Tm2. In the DSC curve, through a straight line, the base line of the whole of the endothermic peaks before the start of the melting was joined with the base line of the same after the end of the melting. From a maximum point present between the highest-temperature point endothermic peak and the endothermic peak adjacent to the highest-temperature point peak, a straight line was drawn in a vertical direction. The area of the region surrounded by the two straight lines and the DSC curve was measured as the higher-temperature point endothermic peak calorie of the PHA mixture.

The higher-temperature point endothermic peak calorie measured by this method is compared with a separately prepared calibration curve to presume the content of a PHB corresponding to the PHA (B) shown by this higher-temperature point endothermic peak calorie. A method for preparing the calibration curve is described hereinafter.

In the same way as in Example 1, which will be detailed later, Cupriavidus necator H16 strain was used to produce a PHB having a melting point of 170° C. or higher. In the same manner, a KNK-631 strain described in JP 2013-9627 A was used to produce a PHBH having a melting point of 130° C. or lower in the same way as in Example 1. Next, the resultant PHB and PHBH were mixed with each other to produce a PHBH/PHB mixture that reproduces a co-product simulatively as follows. First, the PHB and the PHBH were each dissolved in chloroform to give a concentration of 10 g/L to yield a solution of each of the polymers. Next, the individual polymer solutions were mixed with each other to set the ratio by weight of the PHB to the PHBH to 1/99. To 400 mL of hexane was gently added 100 mL of the mixed polymer solution while hexane was stirred. The precipitated polymer was filtrated and separated, and then dried at 60° C. to yield a PHBH/PHB mixture. In the same way, PHBH/PHB mixtures were yielded in which respective ratios by weight of the PHB/the PHBH were 3/97, 5/95, 7/93 and 10/90. The resultant five PHBH/PHB mixtures were each subjected to DSC to measure the calorie of its higher-temperature point endothermic peak. From the resultant individual higher-temperature point endothermic peak calories, a calibration curve was prepared for estimating the PHB content in any PHA mixture.

<Case where Only One Peak is Observed between 85° C. and 180° C. in the Resultant DSC Curve>

In the above-mentioned DSC curve, through a straight line, the base line of the whole of the endothermic peaks before the start of the melting was joined with the base line of the same after the end of the melting, and at 160° C., a straight line was drawn in a vertical direction. The melting calorie in a region of temperature points higher than 160° C. that is surrounded by the two straight lines and the DSC curve was measured.

The melting calorie of the region of the temperature points higher than 160° C., which had been measured in the manner described above, was compared with a separately prepared calibration curve to presume the content of the PHB in the PHA mixture. A method for preparing the calibration curve is as follows.

In the same way as in Example 1, which will be detailed later, Cupriavidus necator H16 strain was used to produce a PHB. In the same manner, a KNK-005 strain described in U.S. Pat. No. 7,384,766 was used to produce a PHBH in the same way as in Example 1. Next, the resultant PHB and PHBH were mixed with each other to produce a PHBH/PHB mixture that reproduces a co-product simulatively as follows. First, the PHB and the PHBH were each dissolved in chloroform to give a concentration of 10 g/L to yield a solution of each of the polymers. Next, the individual polymer solutions were mixed with each other to set the ratio by weight of the PHB to the PHBH to 10/90. To 400 mL of hexane was gently added 100 mL of the mixed polymer solution while hexane was stirred. The precipitated polymer was filtrated and separated, and then dried at 60° C. to yield a PHBH/PHB mixture. In the same way, PHBH/PHB mixtures were yielded in which respective ratios by weight of the PHB/the PHBH are 7/93, 15/85 and 20/80. The resultant four PHBH/PHB mixtures were each subjected to DSC to measure the melting calorie in its region of temperature points higher than 160° C. From the resultant respective melting calories of the regions of the temperature points higher than 160° C., a calibration curve was prepared for estimating the PHB content in any PHA mixture.

Evaluation of PHA Mixture by Annealing Method:

About PHAs obtained by culturing followed by purification, a differential scanning calorimeter (DSC 220, manufactured by SII Nano Technology Inc.) was used to evaluate a PHA mixed state by an annealing method in the following manner:

In a DSC thereof, the temperature of the PHAs, the weight of which was from 4.5 to 5.5 mg, was raised from 23° C. to 160° C. at a rate of 10° C./minute. The PHAs were kept at 160° C. for 30 minutes to be annealed, and then the temperature thereof was lowered to 23° C. at a rate of 10° C./minute. Thereafter, a DSC curve thereof was obtained which is a curve at the time of the heating from 23° C. to 200° C. at the rate of 10° C./minute. In this DSC curve, through a straight line, a point at 60° C. on the DSC curve was joined with the base line after the end of the melting. From a maximum point present between the highest-temperature point endothermic peak and the endothermic peak adjacent to the highest-temperature point peak, a straight line was drawn in a vertical direction. The area of the region surrounded by the two straight lines and the DSC curve was measured as the higher-temperature point endothermic peak calorie.

Evaluation of Crystallization of PHA:

The crystallization of any resultant PHA was evaluated by making a measurement using a differential scanning calorimeter. In the differential scanning calorimetry, the temperature of the PHA, the weight of which was from 2 to 5 mg, was raised from 5° C. to 170° C. at a rate of 10° C./minute. The PHA was kept at this temperature for 5 minutes, and then cooled from 170° C. to 5° C. at a rate of 10° C./minute. From the crystallization peak temperature (Tc) and the crystallization exothermic calorie (Hc) in the resultant exothermic curve, the ease of the crystallization of the PHA was evaluated. As the crystallization peak temperature (Tc) was higher and the crystallization exothermic calorie (Hc) was larger, the PHA was better crystallized.

Measurement of Solidification Period of PHA:

The solidification period of any resultant PHA was measured, using a small-sized compounder (Xplore 5 cc Micro-Compounder, manufactured by DSM). The cylinder set-temperature of the small-sized compounder was set to 150° C. (in each of Examples 1 to 3 and 6, and Comparative Example 1), or 170° C. (in each of Examples 9 to 11, and Comparative Example 2). The PHA was melted and kneaded at a screw rotation number of 100 rpm for 3 minutes (in each of Examples 1 to 3 and 6, and Comparative Example 1), or for 1 minute (in each of Examples 9 to 11, and Comparative Example 2). Thereafter, from a nozzle having a diameter of 3 mm, the melted PHA was discharged into a strand form. The strand-form PHA was immediately immersed in a hot water bath of 55° C. (in each of Examples 1 to 3 and 6, and Comparative Example 1) or 50° C. (in each of Examples 9 to 11, and Comparative Example 2). At this time, a period required until the strand was completely solidified was defined as the solidification period of the PHA. As the solidification period was shorter, the PHA was more rapidly crystallized to be made better in solidification performance.

Production Example 1

Production of KNK-005 ΔphaZ1,2,6 Strain

First, in order to disrupt phaZ6 gene, a plasmid for gene-substitution was produced. A genomic DNA of *C. necator* H16 strain was used as a template to conduct PCR using respective DNAs represented by SEQ ID NOs: 20 and 21 as primers. As a polymerase therefor, a polymerase KOD-plus (manufactured by Toyobo Co., Ltd.) was used. In the same way, PCR was conducted, using respective DNAs represented by SEQ ID NOs: 22 and 23 as primers. Furthermore, the two DNA fragments obtained by the PCR were used as templates to conduct PCR, using respective DNAs represented by SEQ ID NOs: 20 and 23 as primers. The resultant DNA fragment was digested with restriction enzyme SmiI. This DNA fragment was ligated with a DNA fragment obtained by digesting a vector pNS2X-sacB described in JP 2007-259708 A with SmiI, using a DNA ligase (Ligation High, manufactured by Toyobo Co., Ltd.) to produce a gene-disrupting plasmid pNS2X-phaZ6(-+) having upstream and downstream DNA sequences of the structural gene phaZ6.

Next, the gene disrupted strain was produced. The gene-disrupting plasmid pNS2X-phaZ6(-+) was introduced into an *E. coli* S17-1 strain (ATCC47055). The *E. coli* strain and a KNK-005 strain (see U.S. Pat. No. 7,384,766) were mix-cultured on a nutrient agar medium (manufactured by DIFCO) to be subjected to conjugal transfer. The KNK-005 strain is a bacterial strain having a gene encoding a PHA synthase shown in SEQ ID NO: 3, a host of this strain being the *C. necator* H16 strain.

From bacterial strains after the conjugal transfer, the following strain was selected: a bacterial strain growing on a Simmons' citrate agar containing 250 mg/L of kanamycin sulfate (sodium citrate: 2 g/L, sodium chloride: 5 g/L, magnesium sulfate heptahydrate: 0.2 g/L, ammonium dihydrogenphosphate: 1 g/L, dipotassium hydrogenphosphate: 1 g/L, and agar: 1.5 g/L; pH: 6.8). In this way, a strain was obtained in which the plasmid was incorporated into chromosomes of the KNK-005 strain. Two generations of this strain were cultured on Nutrient Broth (manufactured by DIFCO). Thereafter, bacterial strains growing on Nutrient Agar containing 15% of sucrose was selected. From the resultant bacterial strains, PCR was used to screen strains in which the entire length of a sequence from a start codon of the phaZ6 gene to a stop codon thereof was deleted. One of the strains was named a KNK-005ΔphaZ6 strain. The KNK-005ΔphaZ6 strain is a bacterial strain in which the entire length of the phaZ6 gene on any chromosome is deleted and the chromosome has, thereon, a gene encoding a PHA synthase shown in SEQ ID NO: 3.

Next, in order to disrupt phaZ1 gene, a plasmid for gene-substitution was produced. A genomic DNA of *C. necator* H16 strain was used as a template to conduct PCR using respective DNAs represented by SEQ ID NOs: 24 and 25 as primers. As a polymerase therefor, the above-specified KOD-plus was used. In the same way, PCR was conducted, using respective DNAs represented by SEQ ID NOs: 26 and 27 as primers. Furthermore, the two DNA fragments obtained by the PCR were used as templates to conduct PCR, using respective DNAs represented by SEQ ID NOs: 24 and 27 as primers. The resultant DNA fragment was digested with restriction enzyme SmiI. This DNA fragment was ligated with a DNA fragment obtained by digesting the above-specified pNS2X-sacB with SmiI using the above-specified DNA ligase to produce a gene-disrupting plasmid pNS2X-phaZ1(-+) having upstream and downstream DNA sequences of the structural gene phaZ1.

In the same way as used to disrupt the phaZ6 gene, the KNK-005ΔphaZ6 strain was used as a parent strain to disrupt the phaZ1 gene with the pNS2X-phaZ1(-+). The resultant strain was named a KNK-005ΔphaZ1,6 strain. The KNK-005ΔphaZ1,6 strain is a bacterial strain in which the entire length of the phaZ1 gene and that of the phaZ6 gene on any chromosome are deleted and the chromosome has, thereon, a gene encoding a PHA synthase shown in SEQ ID NO: 3.

Next, in order to disrupt phaZ2 gene, a plasmid for gene-substitution was produced. A genomic DNA of *C. necator* H16 strain was used as a template to conduct PCR using respective DNAs represented by SEQ ID NOs: 28 and 29 as primers. As a polymerase therefor, the above-specified KOD-plus was used. In the same way, PCR was conducted, using respective DNAs represented by SEQ ID NOs: 30 and 31 as primers. Furthermore, the two DNA fragments obtained by the PCR were used as templates to conduct PCR, using respective DNAs represented by SEQ ID NOs: 28 and 31 as primers. The resultant DNA fragment was digested with restriction enzyme SmiI. This DNA fragment was ligated with a DNA fragment obtained by digesting the above-specified pNS2X-sacB with SmiI using the above-specified DNA ligase to produce a gene-disrupting plasmid pNS2X-phaZ2(-+) having upstream and downstream DNA sequences of the structural gene phaZ2.

In the same way as used to disrupt the phaZ6 gene, the KNK-005ΔphaZ1,6 strain was used as a parent strain to disrupt the phaZ2 gene with the pNS2X-phaZ2(-+). The resultant strain was named a KNK-005ΔphaZ1,2,6 strain. The KNK-005ΔphaZ1,2,6 strain is a bacterial strain in which the entire length of the phaZ1 gene and that of the phaZ6 gene on any chromosome are deleted, a sequence from a $16^{th}$ codon of the phaZ2 gene to a stop codon thereof was deleted, and the chromosome has, thereon, a gene encoding a PHA synthase shown in SEQ ID NO: 3.

Production Example 2

Production of KNK-005 REP-phaJ4bΔphaZ1,2,6 Strain

Furthermore, in order to insert an expression regulatory sequence for enhancing the expression of a phaJ4b gene into an upstream of the phaJ4b gene on any chromosome, a plasmid for expression regulatory sequence insertion was produced. A genomic DNA of *C. necator* H16 strain was used as a template to conduct PCR using respective DNAs represented by SEQ ID NOs: 32 and 33 as primers. As a polymerase therefor, the above-specified KOD-plus was used. In the same way, PCR was conducted, using respective DNAs represented by SEQ ID NOs: 34 and 35 as primers. Furthermore, in the same way, PCR was conducted, using respective DNAs represented by SEQ ID NOs: 36 and 37 as primers. The three DNA fragments obtained by these PCR were used as templates to conduct PCR, using respective DNAs represented by SEQ ID NOs: 32 and 35 as primers. The resultant DNA fragment was digested with SmiI. This DNA fragment was ligated with a DNA fragment obtained by digesting the above-specified pNS2X-sacB with SmiI using the above-specified DNA ligase to produce a DNA-inserting plasmid pNS2X-sacB+phaJ4bU-REP-phaJ4b having an expression regulatory sequence made of upstream DNA sequence the phaJ4b structure gene, a phaC1 promoter and a phaC1SD sequence, and a part of the phaJ4b structural gene sequence.

In the same way as used to disrupt the above-mentioned genes, the NK-005ΔphaZ1,2,6 strain obtained in Production Example 1 was used as a parent strain to insert an expression regulatory sequence into an upstream side of the phaJ4b gene, using the pNS2X-sacB+phaJ4bU-REP-phaJ4b. The resultant strain was named a KNK-005 REP-phaJ4bΔphaZ1,2,6 strain. The KNK-005 REP-phaJ4bΔphaZ1,2,6 strain is a bacterial strain in which the entire length of the phaZ1 gene and that of the phaZ6 gene on any chromosome are deleted, a sequence from a $16^{th}$ codon of the phaZ2 gene to a stop codon thereof is deleted, the expression regulatory sequence made of the phaC1 promoter (REP) and the phaC1SD sequence (REP-SD) is inserted immediately upstream of the phaJ4b gene, and the chromosome has, thereon, a gene encoding a PHA synthase shown in SEQ ID NO: 3.

Production Example 3

Production of PHB-Producing Plasmid pCUP2-REP-phaC$_{Re}$

A PHB-producing plasmid pCUP2-REP-phaC$_{Re}$ was produced for being introduced into the KNK-005 REP-phaJ4bΔphaZ1,2,6 strain produced in Production Example 2.

First, a genomic DNA of *C. necator* H16 strain was used as a template to conduct PCR using respective DNAs represented by SEQ ID NOs: 38 and 39 as primers. The resultant DNA fragment was digested with EcoRI and SpeI. As a polymerase therefor, the above-specified KOD-plus was used. This DNA fragment was ligated with a DNA fragment obtained by digesting a pCUP2 vector described in JP 2007-259708 A with MunI and SpeI using the above-specified DNA ligase to produce the captioned PHB-producing plasmid pCUP2-REP-phaC$_{Re}$ having an expression regulatory sequence made of a phaC1 promoter and a phaC1SD sequence, and a phaC$_{Re}$ structural gene sequence.

Production Example 4

Production of PHB-Producing Plasmid pCUP2-PJ4a-phaC$_{Re}$

A PHB-producing plasmid pCUP2-PJ4a-phaC$_{Re}$ was produced for being introduced into the KNK-005 REP-phaJ4bΔphaZ1,2,6 strain produced in Production Example 2.

First, a genomic DNA of *C. necator* H16 strain was used as a template to conduct PCR using respective DNAs represented by SEQ ID NOs: 40 and 41 as primers. In the same way, PCR was conducted, using respective DNAs represented by SEQ ID NOs: 39 and 42 as primers. The two DNA fragments obtained by these PCR were used as a template to conduct PCR, using DNAs represented by SEQ ID NOs: 39 and 40 as primers. The resultant DNA fragment was digested with MunI and SpeI. As a polymerase therefor, the above-specified KOD-plus was used. This DNA fragment was ligated with a DNA fragment obtained by digesting the above-specified pCUP2 vector with MunI and SpeI using the above-specified DNA ligase to produce the captioned PHB-producing plasmid pCUP2-PJ4a-phaC$_{Re}$ having an expression regulatory sequence PJ4a, and a phaC$_{Re}$ structural gene sequence.

Production Example 5

Production of PHB-Producing Plasmid pCUP2-Plac-phaC$_{Re}$

A PHB-producing plasmid pCUP2-Plac-phaC$_{Re}$ was produced for being introduced into the KNK-005 REP-phaJ4bΔphaZ1,2,6 strain produced in Production Example 2.

First, a genomic DNA of *C. necator* H16 strain was used as a template to conduct PCR using respective DNAs represented by SEQ ID NOs: 39 and 43 as primers. The resultant DNA fragment was digested with MunI and SpeI. As a polymerase therefor, the above-specified KOD-plus was used. This DNA fragment was ligated with a DNA fragment obtained by digesting the above-specified pCUP2 vector with MunI and SpeI using the above-specified DNA ligase to produce the captioned PHB-producing plasmid pCUP2-SD-phaC$_{Re}$ having an expression regulatory sequence made of a phaC1SD sequence (REP-SD) and a phaC$_{Re}$ structural gene sequence.

Next, a product pCR(R)2.1-TOPO(R) (manufactured by Invitrogen) was used as a template to conduct PCR using respective DNAs represented by SEQ ID NOs: 44 and 45 as primers. The resultant DNA fragment was digested with MunI. As a polymerase therefor, the above-specified KOD-plus was used. This DNA fragment was ligated with a DNA fragment obtained by digesting the pCUP2-SD-phaC$_{Re}$ with MunI using the above-specified DNA ligase to produce the captioned PHB-producing plasmid pCUP2-Plac-phaC$_{Re}$ having an expression regulatory sequence made of a lac promoter and a phaC1SD sequence, and the phaC$_{Re}$ structural gene sequence.

Production Example 6

Production of PHB-Producing Plasmid Introduced Strain, Using KNK-005 REP-phaJ4bΔphaZ1,2,6 Strain Described in Production Example 2 as Parent Strain In order to produce a bacterial strain for co-producing a PHBH and a PHB, the KNK-005 REP-phaJ4bΔphaZ1,2,6 strain produced in Production Example 2 was used as a parent strain to produce a bacterial strain into which the plasmid described in any one of Production Examples 3 to 5 was introduced:

First, the above-specified KNK-005 REP-phaJ4bΔphaZ1, 2,6 strain was cultured overnight in a nutrient broth medium. Into 100 mL of a nutrient broth medium was inoculated 0.5 mL of the resultant culture liquid, and then the strain was cultured at 30° C. for 3 hours. The resultant culture liquid was rapidly cooled on ice. The cells were collected and sufficiently washed with ice-cooled distilled water. Thereafter, the resultant cell pellet was suspended in 2 mL of distilled water. The suspended cells were mixed with each of the plasmid solutions. The mixture was poured into a cuvette to be electroporated. The electroporation was performed, using a Micro Pulser Electroporator (manufactured by Bio-Rad Laboratories, Inc.) under conditions of a voltage of 1.5 kV, a resistance of 800 Ω, and a current of 25 µF. After the electroporation, the cell solution was collected, and thereto was added 5 mL of Nutrient Broth to culture the cells at 30° C. for 3 hours. The resultant culture liquid was applied to Nutrient Agar containing 100 mg/L of kanamycin sulfate. This was cultured at 30° C. for 3 days. From the resultant colonies, a bacterial strain into which each of the plasmids was introduced was obtained. The resultant bacterial strains were named
a KNK-005 REP-phaJ4bΔphaZ1,2,6/pCUP2-Plac-phaC$_{Re}$ strain,
a KNK-005 REP-phaJ4bΔphaZ1,2,6/pCUP2-PJ4a-phaC$_{Re}$ strain, and
a KNK-005 REP-phaJ4bΔphaZ1,2,6/pCUP2-REP-phaC$_{Re}$ strain, respectively Production Example 7

Production of KNK-005 Ptrp-phaJ4aΔphaZ1::PJ4a-phaC$_{Re}$ΔphaZ2,6 Strain

In order to insert an expression regulatory sequence into an upstream side of a phaJ4a gene on any chromosome, an expression regulatory sequence insertion plasmid was produced. A genomic DNA of *C. necator* H16 strain was used as a template to conduct PCR using respective DNAs represented by SEQ ID NOs: 46 and 47 as primers. As a polymerase therefor, the above-specified KOD-plus was used. In the same way, PCR was conducted, using respective DNAs represented by SEQ ID NOs: 48 and 49 as primers. Furthermore, a plasmid pKK388-1 (manufactured by Clontech Laboratories, Inc.) was used as a template to conduct PCR using respective DNAs represented by SEQ ID NOs: 50 and 51 as primers. The three DNA fragments obtained by these PCR were used as templates to conduct PCR, using respective DNAs represented by SEQ ID NOs: 46 and 49 as primers. The resultant DNA fragment was digested with SmiI. This DNA fragment was ligated with a DNA fragment obtained by digesting the above-specified pNS2X-sacB with SmiI using the above-specified DNA ligase to produce a DNA-inserting plasmid pNS2X-sacB+phaJ4aU-trp-phaJ4a having an upstream DNA sequence of the phaJ4a structural gene, i.e., an expression regulatory sequence made of a trp promoter and a phaC1SD sequence, and a part of the phaJ4a structural gene sequence.

In the same way as used in Production Example 2, the above-specified KNK-005ΔphaZ1,2,6 strain was used as a parent strain to insert an expression regulatory sequence into an upstream of the phaJ4a gene, using the pNS2X-sacB4-phaJ4aU-trp-phaJ4a. The resultant strain was named a KNK-005 Pfrp-phaJ4aΔphaZ1,2,6 strain. The KNK-005 Ptrp-phaJ4aΔphaZ1,2,6 strain is a bacterial strain in which the entire length of the phaZ1 gene and that of the phaZ6 gene on any chromosome are deleted, a sequence from a 16$^{th}$ codon of the phaZ2 gene to a stop codon thereof is deleted, the expression regulatory sequence made of the trp promoter and the phaC1SD sequence is inserted immediately upstream of the phaJ4a gene, and the chromosome has, thereon, a gene encoding a PHA synthase shown in SEQ ID NO: 3.

Next, in order to introduce a PHB-producing gene expression cassette into a phaZ1-gene-deleted region of the KNK-005 Ptrp-phaJ4aΔphaZ1,2,6 strain, a DNA-inserting plasmid was produced. First, a genomic DNA of *C. necator* H16 strain was used as a template to conduct PCR using respective DNAs represented by SEQ ID NOs: 24 and 52 as primers. As a polymerase therefor, the above-specified KOD-plus was used. In the same way, PCR was conducted, using respective DNAs represented by SEQ ID NOs: 27 and 53 as primers. The two DNA fragments obtained by the PCR were used as templates to conduct PCR, using respective DNAs represented by SEQ ID NOs: 24 and 27 as primers. The resultant DNA fragment was digested with SmiI. This DNA fragment was ligated with a DNA fragment obtained by digesting the above-specified pNS2X-sacB with SmiI using the above-specified DNA ligase to produce a DNA-inserting plasmid pNS2X-sacB-dZ1UL having an upstream DNA sequence of the phaZ1 structural gene, i.e., a DNA sequence shown in SEQ ID NO: 62, and a downstream DNA sequence of the phaZ1 structural gene.

Next, a DNA fragment obtained by digesting the pCUP2-PJ4a-phaC$_{Re}$ produced in Production Example 4 with MunI and SpeI was ligated with a DNA fragment obtained by digesting the pNS2X-sacB-dZ1UL with MunI and SpeI using the above-specified DNA ligase to produce a DNA-inserting plasmid pNS2X-sacB-dZ1UL-PJ4a-phaC$_{Re}$ having an upstream DNA sequence of the phaZ1 structural gene, i.e., an expression regulatory sequence PJ4a, a phaC$_{Re}$ structural gene sequence, and a downstream DNA sequence of the phaZ1 structural gene.

In the same way as used in Production Example 2, the above-specified KNK-005 Ptrp-phaJ4aΔphaZ1,2,6 strain was used as a parent strain to insert a PHB-producing gene expression cassette into its phaZ1-gene-deleted region, using the pNS2X-sacB-dZ1UL-PJ4a-phaC$_{Re}$. The resultant strain was named a KNK-005 Ptrp-phaJ4aΔphaZ1::PJ4a-phaC$_{Re}$ΔphaZ2,6 strain. The KNK-005 Ptrp-phaJ4aΔphaZ1::PJ4a-phaC$_{Re}$ΔphaZ2,6 strain is a bacterial strain in which the entire length of the phaZ1 gene and that of the phaZ6 gene on any chromosome are deleted, a sequence from a 16$^{th}$ codon of the phaZ2 gene to a stop codon thereof is deleted, an expression regulatory sequence made of the trp promoter and the phaC1SD (REP-SD) sequence is inserted immediately upstream of the phaJ4a, the PJ4a, which is an expression regulatory sequence, and the phaC$_{Re}$ structural gene sequence are inserted into the phaZ1-gene-deleted region, and the chromosome has, thereon, a gene encoding a PHA synthase shown in SEQ ID NO: 3.

Production Example 8

Production of KNK-005 REP-phaJ4bΔphaZ1::Plac-phaC$_{Re}$ΔphaZ2,6 Strain

In order to introduce a PHB-producing gene expression cassette into a phaZ1-gene-deleted region of the KNK-005 REP-phaJ4bΔphaZ1,2,6 strain produced in Production Example 2, a DNA-inserting plasmid was produced. First, the above-specified plasmid pCUP2-Plac-phaC$_{Re}$ was used as a template to conduct PCR using respective DNAs represented by SEQ ID NOs: 63 and 39 as primers. The resultant fragment was digested with EcoRI and SpeI, and then ligated with a DNA fragment obtained by digesting the above-specified pNS2X-sacB-dZ1UL with MunI and SpeI through the above-specified DNA ligase to produce a DNA-inserting plasmid pNS2X-sacB-dZ1UL-Plac-phaC$_{Re}$ having an upstream DNA sequence of the phaZ1 structural gene, i.e., an expression regulatory sequence made of a lac promoter and a phaC1SD (REP-SD), a phaC$_{Re}$ structural gene sequence, and a downstream DNA sequence of the phaZ1 structural gene.

In the same way as used in Production Example 2, the above-specified KNK-005 REP-phaJ4bΔphaZ1,2,6 strain was used as a parent strain to insert a PHB-producing gene expression cassette into its phaZ1-gene-deleted region, using the pNS2X-sacB-dZ1UL-Plac-phaC$_{Re}$. The resultant strain was named a KNK-005 REP-phaJ4bΔphaZ1::Plac-phaC$_{Re}$ΔphaZ2,6 strain. The KNK-005 REP-phaJ4bΔphaZ1::Plac-phaC$_{Re}$ΔphaZ2,6 strain is a bacterial strain in which the entire length of the phaZ1 gene and that of the phaZ6 gene on any chromosome are deleted, a sequence from a 16$^{th}$ codon of the phaZ2 gene to a stop codon thereof is deleted, an expression regulatory sequence made of a REP promoter and the phaC1SD (REP-SD) sequence is inserted to a direct upstream side of the phaJ4b gene, the lac promoter, the phaC1SD (REP-SD) sequence, the phaC$_{Re}$ structural gene sequence are inserted into the phaZ1-gene-deleted region, and the chromosome has, thereon, a gene encoding a PHA synthase shown in SEQ ID NO: 3.

Production Example 9

Production of KNK-005 REP-phaJ4bΔphaZ1::PlacN15SDM-phaC$_{Re}$ΔphaZ2,6 Strain

In order to introduce a PHB-producing gene expression cassette into a phaZ1-gene-deleted region of the KNK-005 REP-phaJ4bΔphaZ1,2,6 strain produced in Production Example 2, a DNA-inserting plasmid was produced. First, a genomic DNA of *C. necator* H16 strain was used as a template to conduct PCR using respective DNAs represented by SEQ ID NOs: 64 and 39 as primers. The resultant fragment was digested with MunI and SpeI, and then ligated with a DNA fragment obtained by digesting the above-specified pNS2X-sacB-dZ1UL with MunI and SpeI through the above-specified DNA ligase to produce a DNA-introducing plasmid pNS2X-sacB-dZ1UL-SDM-phaC$_{Re}$ having an upstream DNA sequence of a phaZ1 structural gene, i.e., an expression regulatory sequence made of REP-SDM, a phaC$_{Re}$ structural gene sequence, and a downstream DNA sequence of the phaZ1 structural gene.

Next, the above-specified pCUP2-Plac-phaC$_{Re}$ was used as a template to conduct PCR using respective DNAs represented by SEQ ID NOs: 44 and 65 as primers. In the same way, PCR was conducted, using respective DNAs represented by SEQ ID NOs: 66 and 45 as primers. The two DNA fragments obtained by the PCR were used as templates to conduct PCR, using respective DNAs represented by SEQ ID NOs: 44 and 45 as primers. The resultant DNA fragment was digested with MunI. This DNA fragment was ligated with a DNA fragment obtained by digesting the pNS2X-sacB-dZ1UL-SDM-phaC$_{Re}$ with MunI using the above-specified DNA ligase to produce a DNA-inserting plasmid pNS2X-sacB-dZ1UL-PlacN15SDM-phaC$_{Re}$ having an upstream DNA sequence of the phaZ1, i.e., an expression regulatory sequence made of a lacN15 promoter and the REP-SDM, the phaC$_{Re}$ structural gene sequence, and a downstream DNA sequence of the phaZ1 structural gene.

In the same way as used in Production Example 2, the above-specified KNK-005 REP-phaJ4bΔphaZ1,2,6 strain was used as a parent strain to insert a PHB-producing gene expression cassette into its phaZ1-gene-deleted region, using the pNS2X-sacB-dZ1UL-PlacN15SDM11-phaC$_{Re}$. The resultant strain was named a KNK-005 REP-phaJ4bΔphaZ1::PlacN15SDM-phaC$_{Re}$ΔphaZ2,6 strain. The KNK-005 REP-phaJ4bΔphaZ1::PlacN15SDM-phaC$_{Re}$ΔphaZ2,6 strain is a bacterial strain in which the entire length of the phaZ1 gene and that of the phaZ6 gene on any chromosome are deleted, a sequence from a 16$^{th}$ codon of the phaZ2 gene to a stop codon thereof is deleted, the expression regulatory sequence made of the REP promoter and the phaC1SD (REP-SD) sequence is inserted immediately upstream of the phaJ4b gene, the expression regulatory sequence made of the lacN15 promoter and the REP-SDM sequence, and the phaC$_{Re}$ structural gene sequence are inserted into the phaZ1-gene-deleted region, and the chromosome has, thereon, a gene encoding a PHA synthase shown in SEQ ID NO: 3.

Production Example 10

Production of KNK-005 REP-phaJ4bΔphaZ1::PlacN19SDM-phaC$_{Re}$ΔphaZ2,6 Strain

In order to introduce a PHB-producing gene expression cassette into a phaZ1-gene-deleted region of the KNK-005

REP-phaJ4bΔphaZ1,2,6 strain produced in Production Example 2, a DNA-inserting plasmid was produced. The above-specified pCUP2-Plac-phaC$_{Re}$ was used as a template to conduct PCR using respective DNAs represented by SEQ ID NOs: 44 and 67 as primers. In the same way, PCR was conducted, using respective DNAs represented by SEQ ID NOs: 66 and 45 as primers. The two DNA fragments obtained by the PCR were used as templates to conduct PCR, using respective DNAs represented by SEQ ID NOs: 44 and 45 as primers. The resultant DNA fragment was digested with MunI. This DNA fragment was ligated with a DNA fragment obtained by digesting the above-specified pNS2X-sacB-dZ1UL-SDM-phaC$_{Re}$ with MunI using the above-specified DNA ligase to produce a DNA-inserting plasmid pNS2X-sacB-dZ1UL-PlacN19SDM-phaC$_{Re}$ having an upstream DNA sequence of the phaZ1 structural gene, i.e., an expression regulatory sequence made of a lacN19 promoter and REP-SDM, a phaC$_{Re}$ structural gene sequence, and a downstream DNA sequence of the phaZ1 structural gene.

In the same way as used in Production Example 2, the above-specified KNK-005 REP-phaJ4bΔphaZ1,2,6 strain was used as a parent strain to insert a PHB-producing gene expression cassette into its phaZ1-gene-deleted region, using the pNS2X-sacB-dZ1UL-PlacN19SDM11-phaC$_{Re}$. The resultant strain was named a KNK-005 REP-phaJ4bΔphaZ1::PlacN19SDM-phaC$_{Re}$ΔphaZ2,6 strain. The KNK-005 REP-phaJ4bΔphaZ1::PlacN19SDM-phaC$_{Re}$ΔphaZ2,6 strain is a bacterial strain in which the entire length of the phaZ1 gene and that of the phaZ6 gene on any chromosome are deleted, a sequence from a 16$^{th}$ codon of the phaZ2 gene to a stop codon thereof is deleted, an expression regulatory sequence made of a REP promoter and a phaC1SD (REP-SD) sequence is inserted immediately upstream of the phaJ4b gene, the lacN19 promoter, the REP-SDM sequence, and the phaC$_{Re}$ structural gene sequence are inserted into the phaZ1-gene-deleted region, and the chromosome has, thereon, a gene encoding a PHA synthase shown in SEQ ID NO: 3.

Example 1

Production of PHA Mixture by KNK-005 REP-phaJ4bΔphaZ1,2,6/pCUP2-Plac-phaC$_{Re}$ Strain The KNK-005 REP-phaJ4bΔphaZ1,2,6/pCUP2-Plac-phaC$_{Re}$ strain obtained in Production Example 6 was cultured and purified under conditions described below to produce a PHA mixture. The proportion of the 3HH monomer in the resultant PHA mixture was 10.1% by mole.

The resultant PHA mixture was evaluated by the annealing method, so that the higher-temperature point endothermic peak calorie thereof was 2.2 J/g.

Furthermore, about the resultant PHA mixture, the PHA blend ratio was analyzed, the crystallization was evaluated, and the solidification period was measured. The obtained results are shown in Tables 1 and 2.

Culturing:

The bacterial strains were cultured as follows.

The composition of the seed medium was adjusted to 1% (w/v) of a meat extract, 1% (w/v) of bacto tryptone, 0.2% (w/v) of a yeast extract, 0.9% (w/v) of disodium hydrogenphosphate dodecahydrate and 0.15% (w/v) of potassium dihydrogenphosphate, 50 µg/L kanamycin and the pH thereof was set to 6.8.

The composition of the preculture medium was adjusted to 1.1% (w/v) disodium hydrogenphosphate dodecahydrate, 0.19% (w/v) of potassium dihydrogenphosphate, 1.29% (w/v) of ammonium sulfate, 0.1% (w/v) of magnesium sulfate heptahydrate, 0.5% (v/v) of a solution of trace metals (solution obtained by dissolving, in 0.1 N hydrochloric acid, 1.6% (w/v) of iron(II) chloride hexahydrate, 1% (w/v) of calcium chloride dihydrate, 0.02% (w/v) of cobalt chloride hexahydrate, 0.016% (w/v) of copper sulfate pentahydrate, and 0.012% (w/v) of nickel chloride hexahydrate), and 50 µg/L of kanamycin. As the carbon source, palm double olein oil was used at a concentration of 2.5% (w/v).

The composition of the PHA producing medium was adjusted to 0.578% (w/v) of sodium dihydrogenphosphate dodecahydrate, 0.101% (w/v) of potassium dihydrogenphosphate, 0.437% (w/v) of ammonium sulfate, 0.15% (w/v) of magnesium sulfate heptahydrate, and 0.75% (v/v) of a solution of trace metals (solution obtained by dissolving, in 0.1 N hydrochloric acid, 1.6% (w/v) of iron(II) chloride hexahydrate, 1% (w/v) of calcium chloride dihydrate, 0.02% (w/v) of cobalt chloride hexahydrate, 0.016% (w/v) of copper sulfate pentahydrate, and 0.012% (w/v) of nickel chloride hexahydrate). As the carbon source, the following was used: a substance obtained by emulsifying, through steps described below, a palm fatty acid distillate (PFAD, available from Malaysian Biotechnology Corporation SDN BDH; free fatty acid content: 95.0%; fatty acid composition: C12:0 0.2%, C14:0 1.2%. C16:0 47.6%, C16:1 0.3%, C18:1 35.7%. C18:2 9.7%. C18:3 0.4%, C20:0 0.4%; melting point: 43.8° C.).

The PFAD was weighed out by 550 g, and water was weighed out by 450 g. These components were each heated to 60° C. Thereafter, in the water were dissolved 4.7 g of disodium hydrogenphosphate dodecahydrate and 2.75 g of sodium casein. After the dissolution, the water was mixed with the PFAD, and the mixture was preliminarily emulsified, using a homo-mixer (LABORATORY MIXER EMULSIFIER, manufactured by Silverson Machines Ltd.) at a stirring number of 2500 rpm. Furthermore, this preliminary emulsion was subjected to emulsifying operation at a pressure of 10 bar by a high-pressure homogenizer (PAND2K model, manufactured by Niro Soavi) to yield an emulsion.

Into 10 mL of the seed medium was inoculated 50 µL of a glycerol stock of each of the bacterial strains, and the strain was cultured for 24 hours. The strain was inoculated in an amount of 1.0% (v/v) into a 3-L jar fermenter (MDL-300 model, manufactured by B. E. Mambishi Co., Ltd.) into which 1.8 L of the preculture medium was put. The driving conditions were set as follows: a culturing temperature of 30° C., a stirring speed of 500 rpm, and an air flow rate of 1.8 L/minute. While the pH was controlled between 6.7 and 6.8, the strain was cultured for 28 hours. For the pH control, a 7% aqueous ammonium hydroxide solution was used.

For PHA production and culturing, the precultured yeast was inoculated in an amount of 25% (v/v) into a 10-L jar fermenter (MDL-1000 model, manufactured by B. E. Marubishi Co., Ltd.) into which 2 L of the PHA producing medium was put. The driving conditions were set as follows: a culturing temperature of 32° C., a stirring speed of 450 rpm, and an air flow rate of 3.0 L/minute. The pH was controlled between 6.7 and 6.8. For the pH control, a 7% aqueous ammonium hydroxide solution was used. The culturing was continued for 45 to 54 hours.

Purification:

When the culturing was advanced and then ended, the culture broth was sampled. The cells were collected therefrom by centrifugation, washed with ethanol, and then vacuum-dried to give dry cells.

To 1 g of the resultant dry cells was added 100 mL of chloroform, and the resultant was stirred at room temperature for a whole day and night to extract PHAs inside the cells. The cell residue was removed by filtration, and then an evaporator was used to concentrate the PHAs to a total volume of 30 mL. Thereafter, thereto was slowly added 90 mL of hexane, and then the resultant was gently stirred for 1 hour. The precipitated PHAs were recovered by filtration, and the PHAs were vacuum-dried at 50° C. for 3 hours to give the PHAs as purified PHAs.

Example 2

Production of PHA Mixture by KNK-005 REP-phaJ4bΔphaZ1,2,6/pCUP2-PJ4a-phaC$_{Re}$ Strain A PHA mixture was produced in the same way as in Example 1 except that instead of the KNK-005 REP-phaJ4bΔphaZ1,2,6/pCUP2-Plac-phaC$_{Re}$ strain, the KNK-005 REP-phaJ4bΔphaZ1,2,6/pCUP2-PJ4a-phaC$_{Re}$ strain produced in Production Example 6 was used. The 3HH monomer proportion in the resultant PHA mixture was 11.5% by mole.

Moreover, the resultant PHA mixture was evaluated by the annealing method, so that the higher-temperature point endothermic peak calorie thereof was 3.7 J/g.

Furthermore, about the resultant PHA mixture, the PHA blend ratio was analyzed, the crystallization was evaluated, and the solidification period was measured. The obtained results are shown in Tables 1 and 2. A DSC curve of the resultant PHA mixture is shown in FIG. 1.

Example 3

Production of PHA Mixture by KNK-005 REP-phaJ4bΔphaZ1,2,6/pCUP2-REP-phaC$_{Re}$ Strain A PHA mixture was produced in the same way as in Example 1 except that instead of the KNK-005 REP-phaJ4bΔphaZ1,2,6/pCUP2-Plac-phaC$_{Re}$ strain, the KINK-005 REP-phaJ4bΔphaZ1,2,6/pCUP2-REP-phaC$_{Re}$ strain produced in Production Example 6 was used. The 3HH monomer proportion in the resultant PHA mixture was 9.9% by mole.

Moreover, the resultant PHA mixture was evaluated by the annealing method, so that the higher-temperature point endothermic peak calorie thereof was 9.5 J/g.

Furthermore, about the resultant PHA mixture, the PHA blend ratio was analyzed, the crystallization was evaluated, and the solidification period was measured. The obtained results are shown in Tables 1 and 2.

Example 4

Production of PHA Mixture by KNK-005 Ptrp-phaJ4aΔphaZ1::PJ4a-phaC$_{Re}$ΔphaZ2,6 Strain A PHA mixture was produced in the same way as in Example 1 except that instead of the KNK-005 REP-phaJ4bΔphaZ1,2,6/pCUP2-Plac-phaC$_{Re}$ strain, the KNK-005 Ptrp-phaJ4aΔphaZ1::PJ4a-phaC$_{Re}$ΔphaZ2,6 strain produced in Production Example 7 was used. The 3HH monomer proportion in the resultant PHA mixture was 11.5% by mole. Furthermore, about the resultant PHA mixture, the PHA blend ratio was analyzed. The obtained results are shown in Table 1.

Example 5

Production of PHA Mixture by KNK-005 REP-phaJ4bΔphaZ1,2,6/pCUP2-REP-phaC$_{Re}$ Strain A PHA mixture was produced in the same way as in Example 1 except that instead of the KNK-005 REP-phaJ4bΔphaZ1,2,6/pCUP2-Plac-phaC$_{Re}$ strain, the KNK-005 REP-phaJ4bΔphaZ1,2,6/pCUP2-REP-phaC$_{Re}$ strain produced in Production Example 6 was used. As the carbon source during the culturing, a palm double olein oil was used instead of the emulsified PFAD. The 3HH monomer proportion in the resultant PHA mixture was 11.5% by mole. Furthermore, about the resultant PHA mixture, the PHA blend ratio was analyzed. The obtained result is shown in Table 1. A DSC curve of the resultant PHA mixture is shown in FIG. 2.

Example 6

Production of PHA Mixture by KNK-005 REP-phaJ4bΔphaZ1::Plac-phaC$_{Re}$ΔphaZ2,6 Strain A PHA mixture was produced in the same way as in Example 1 except that instead of the KNK-005 REP-phaJ4bΔphaZ1,2,6/pCUP2-Plac-phaC$_{Re}$ strain, the KNK-005 REP-phaJ4bΔphaZ1::Plac-phaC$_{Re}$ΔphaZ2,6 strain produced in Production Example 8 was used. For the culturing, a medium to which no kanamycin was added was used. As the carbon source during the culturing, palm oil was used instead of the emulsified PFAD. The 3HH monomer proportion in the resultant PHA mixture was 11.0% by mole. Furthermore, about the resultant PHA mixture, the PHA blend ratio was analyzed. The obtained results are shown in Tables 1 and 2. Moreover, the PHA mixture was evaluated by the annealing method. As a result, the higher-temperature point endothermic peak calorie thereof was 4.5 J/g. From the numerical value of the higher-temperature point endothermic peak calorie obtained by the annealing method, a presumed value of the PHB content was obtained, using a separately prepared calibration curve (about a PHBH/PHB mixture reproducing the co-product simulatively, the higher-temperature point endothermic peak calorie thereof was measured by the annealing method). As a result, the presumed PHB content was 4.2% by weight. Thus, it was verified that this value was identical with the numerical value obtained from the DSC result in the case where no annealing was conducted.

Example 7

Production of PHA Mixture by KNK-005 REP-phaJ4bΔphaZ1::PlacN15SDM-phaC$_{Re}$ΔphaZ2,6 Strain A PHA mixture was produced in the same way as in Example 6 except that instead of the KNK-005 REP-phaJ4bΔphaZ1::Plac-phaC$_{Re}$ΔphaZ2,6 strain, the KNK-005 REP-phaJ4bΔphaZ1::PlacN15SDM-phaC$_{Re}$ΔphaZ2,6 strain produced in Production Example 9 was used. The 3HH monomer proportion in the resultant PHA mixture was 10.8% by mole. Furthermore, about the resultant PHA mixture, the PHA blend ratio was analyzed. The obtained result is shown in Table 1.

Example 8

Production of PHA Mixture by KNK-005 REP-phaJ4bΔphaZ1::PlacN19SDM-phaC$_{Re}$ΔphaZ2,6 Strain A PHA mixture was produced in the same way as in Example 6 except that instead of the KNK-005 REP-phaJ4bΔphaZ1::Plac-phaC$_{Re}$ΔphaZ2,6 strain, the KNK-005 REP-phaJ4bΔphaZ1::Plac19SDM-phaC$_{Re}$ΔphaZ2,6 strain produced in Production Example 10 was used. The 3HH monomer proportion in the resultant PHA mixture was 10.3% by mole. Furthermore, about the resultant PHA mixture, the PHA blend ratio was analyzed. The obtained result is shown in Table 1.

Comparative Example 1

Production of PHA by KNK-005 REP-phaJ4bΔphaZ1,2,6 Strain

A PHA was produced in the same way as in Example 1 except that instead of the KNK-005 REP-phaJ4bΔphaZ1,2, 6/pCUP2-Plac-phaC$_{Re}$ strain, the KNK-005 REP-phaJ4bΔphaZ1,2,6 strain produced in Production Example 2 was used. The 3HH monomer proportion in the resultant PHA, that is, PHBH was 10.4% by mole. Furthermore, about the resultant PHA, the PHA blend ratio was analyzed, the crystallization was evaluated, and the solidification period was measured. The obtained results are shown in Tables 1 and 2. A DSC curve of the resultant PHA is shown in FIG. 3. Thus, it is understood that the endothermic peak ends at about 143° C., and no PHB is produced so that no higher-temperature point endothermic peak is present.

TABLE 1

| | Bacterial strain name | Tm1 (° C.) | Tm2 (° C.) | Higher-temperature-point calorie (J/g) | Presumed PHB content (wt %) |
|---|---|---|---|---|---|
| Example 1 | KNK-005 REP-phaJ4b Δ phaZ1,2,6/pCUP2-Plac-phaC$_{Re}$ | 110 | 154 | 2.6 | 2.6 |
| Example 8 | KNK-005 REP-phaJ4b Δ phaZ1::PlacN19SDM-phaC$_{Re}$Δ phaZ2,6 | 114 | 163 | 3.7 | 3.4 |
| Example 7 | KNK-005 REP-phaJ4b Δ phaZ1::PlacN15SDM-phaC$_{Re}$Δ phaZ2,6 | 108 | 165 | 4.3 | 3.8 |
| Example 2 | KNK-005 REP-phaJ4b Δ phaZ1,2,6/pCUP2-PJ4a-phaC$_{Re}$ | 100 | 154 | 4.3 | 3.8 |
| Example 6 | KNK-005 REP-phaJ4b Δ phaZ1::Plac-phaC$_{Re}$ΔphaZ2,6 | 107 | 157 | 4.9 | 4.2 |
| Example 4 | KNK-005 Ptrp-phaJ4a Δ phaZ1::PJ4a-phaC$_{Re}$ΔphaZ2,6 | 101 | 163 | 6.4 | 5.4 |
| Example 3 | KNK-005 REP-phaJ4b Δ phaZ1,2,6/pCUP2-REP-phaC$_{Re}$ | 108 | 156 | 10.9 | 8.7 |
| Example 5 | KNK-005 REP-phaJ4b Δ phaZ1,2,6/pCUP2-REP-phaC$_{Re}$ | 99 | 162 | 15.9 | 12.4 |
| Comparative Example 1 | KNK-005 REP-phaJ4b Δ phaZ1,2,6 | 107 | — | — | 0 |

As shown in Table 1, it was observed that in Comparative Example 1, no endothermic peak appeared around 155° C. while in Examples 1 to 8, an endothermic peak appeared around a temperature from 154° C. to 165° C. From this matter, it has been confirmed that a PHBH and a PHB are co-produced in the same cell by the introduction of a PHB-producing gene cassette as described above. The higher-temperature point endothermic peak (Tm2) appeared in each of Examples 1 to 8 originated from the PHB; however, the melting point of the PHB is originally 175° C. Thus, it has been verified that the mixing of the PHB with the PHBH, which is lower in melting point, causes the melting point of the PHB to be shifted toward lower temperatures. The higher-temperature point endothermic peak calorie and the presumed content of the PHB were changed in accordance with the expression regulatory sequence to which the phaC$_{Re}$ gene was linked, the introduction mode of the phaC$_{Re}$ gene, and the carbon source. It has been verified that the 3HH monomer proportion in the PHBH in the PHA mixture obtained in each of Examples 1 to 8 is from about 10 to 13% by mole from the 3HH monomer proportion and the PHB presumed content in the PHA mixture.

TABLE 2

| | Bacterial strain name | Crystallization peak temperature (Tc) (° C.) | Crystallization exothermic calorie (Hc) (J/g) | Solidification period (second) |
|---|---|---|---|---|
| Example 1 | KNK-005 REP-phaJ4b Δ phaZ1,2,6/pCUP2-Plac-phaC$_{Re}$ | 76 | 30 | 42 |

TABLE 2-continued

| Bacterial strain name | | Crystallization peak temperature (Tc) (° C.) | Crystallization exothermic calorie (Hc) (J/g) | Solidification period (second) |
|---|---|---|---|---|
| Example 2 | KNK-005 REP-phaJ4b Δ phaZ1,2,6/pCUP2-PJ4a-phaC$_{Re}$ | 75 | 24 | 57 |
| Example 6 | KNK-005 REP-phaJ4b Δ phaZ1::Plac-phaC$_{Re}$ΔphaZ2,6 | 77 | 27 | 53 |
| Example 3 | KNK-005 REP-phaJ4b Δ phaZ1,2,6/pCUP2-REP-phaC$_{Re}$ | 97 | 34 | 32 |
| Comparative Example 1 | KNK-005 REP-phaJ4b Δ phaZ1,2,6 | 56 | 14 | 117 |

As shown in Table 2, when Examples 1 to 3 and 6 are compared with Comparative Example 1, the crystallization peak temperature Tc was changed toward higher temperatures so that the crystallization exothermic calorie Hc was increased. The solidification period of Examples 1 to 3 and 6 were two or more times shorter than that of Comparative Example 1. From these results, it has been verified that according to the co-production of a PHBH and a PHB, the crystallization/solidification speed of the polymers is largely improved.

Production Example 11

Production of PHB-Producing Plasmid pCUP2-PlacUV5-phaC$_{Re}$

A PHB-producing plasmid pCUP2-PlacUV5-phaC$_{Re}$ was produced for introduction into the KNK-005ΔphaZ1,2,6 strain produced in Production Example 1.

First, a genomic DNA of a *C. necator* H16 strain was used as a template to conduct PCR using respective DNAs represented by SEQ ID NOs: 54 and 55 as primers. The resultant DNA fraction was digested with MunI. As a polymerase therefor, the above-specified KOD-plus was used. This DNA fragment was ligated with a DNA fragment obtained by digesting the pCUP2-SD-phaC$_{Re}$ produced in Production Example 5 with MunI, using the above-specified DNA ligase to produce the captioned PHB-producing plasmid pCUP2-PlacUV5-phaC$_{Re}$ having an expression regulatory sequence made of a lacUV5 promoter and a phaC1SD sequence, and a phaC$_{Re}$ structural gene sequence.

Production Example 12

Production of Strain for Introduction of PHB-Producing Plasmid, Using KNK-005ΔphaZ1,2,6 Strain Produced in Production Example 1 as Parent Strain In order to produce a bacterial strain for co-producing a PHBH and a PHB, the KNK-005ΔphaZ1,2,6 strain produced in Production Example 1 was used as a parent strain to produce a bacterial strain into which the plasmid described in either one of Production Examples 3 and 11 was introduced.

First, the KNK-005ΔphaZ1,2,6 strain was cultured overnight in a nutrient broth medium. Into 100 mL of a nutrient broth medium was inoculated 0.5 mL of the resultant culture liquid, and then the strain was cultured at 30° C. for 3 hours. The resultant culture liquid was rapidly cooled on ice. The cells were collected and sufficiently washed with ice-cooled distilled water. Thereafter, the resultant cells were suspended in 2 mL of distilled water. The cells were mixed with each of the plasmid solutions. The mixture was poured into a cuvette to be electroporated. The electroporation was performed, using a Micro Pulser Electroporator (manufactured by Bio-Rad Laboratories, Inc.) under conditions of a voltage of 1.5 kV, a resistance of 800 Ω, and a current of 25 mF. After the electroporation, the cell solution was collected, and thereto was added 5 mL of a nutrient broth medium to culture the cells at 30° C. for 3 hours. The resultant culture liquid was applied to a nutrient agar medium containing 100 mg/L of kanamycin sulfate. This was cultured at 30° C. for 3 days. From the resultant colonies, a bacterial strain into which each of the plasmids was introduced was obtained. The resultant bacterial strains were named a KNK-005ΔphaZ1,2,6/pCUP2-REP-phaC$_{Re}$ strain and a KNK-005ΔphaZ1,2,6/pCUP2-PlacUV5-phaC$_{Re}$ strain, respectively.

Production Example 13

Production of KNK-005ΔphaZ1::Plac-phaC$_{Re}$ΔphaZ2,6 Strain

A strain was produced in which a PHB-producing gene expression cassette was introduced into a region where the phaZ1 gene of the KNK-005ΔphaZ1,2,6 strain produced in Production Example 1 was deleted.

In the same way as used in Production Example 2, the KNK-005ΔphaZ1,2,6 strain was used as a parent strain to insert a PHB-producing gene expression cassette into its phaZ1-gene-deleted region, using the pNS2X-sacB-dZ1UL-Plac-phaC$_{Re}$ described in Production Example 8. The resultant strain was named a KNK-005ΔphaZ1::Plac-phaC$_{Re}$ΔphaZ2,6 strain. The KNK-005ΔphaZ1::Plac-phaC$_{Re}$ΔphaZ2,6 strain was a bacterial strain in which the entire length of the phaZ1 gene and that of the phaZ6 gene on any chromosome are deleted, a sequence from a 16$^{th}$ codon of the phaZ2 gene to a stop codon thereof is deleted, a lac promoter, a phaC1SD (REP-SD) sequence, and a phaC$_{Re}$ structural gene sequence are inserted into the phaZ1-gene-deleted region, and the chromosome has, thereon, a gene encoding a PHA synthase shown in SEQ ID NO: 3.

Example 9

Production of PHA Mixture, Using KNK-005 ΔphaZ1,2,6/pCUP2-REP-phaC$_{Re}$ Strain A PHA mixture was produced in the same way as in Example 1 except that instead of the KNK-005 REP-phaJ4bΔphaZ1,2,6/pCUP2-Plac-phaC$_{Re}$ strain, the KNK-005ΔphaZ1,2,6/pCUP2-REP-phaC$_{Re}$ strain produced in Production Example 12 was used. The 3HH monomer proportion in the resultant PHA mixture was 4.8% by mole. Furthermore, about the resultant PHA mixture, the PHA blend ratio was analyzed, an evaluation was made by the annealing method, and the solidification period was measured. The obtained results are shown in Table 3. A DSC curve of the resultant PHA mixture is shown in FIG. 4, and a DSC curve of a product obtained by annealing the mixture by the annealing method is shown in FIG. 5.

Example 10

Production of PHA Mixture, Using KNK-005ΔphaZ1,2,6/pCUP2-PlacUV5-phaC$_{Re}$ Strain A PHA mixture was produced in the same way as in Example 1 except that instead of the KNK-005 REP-phaJ4b ΔphaZ1,2,6/pCUP2-Plac-phaC$_{Re}$ strain, the KNK-005ΔphaZ1,2,6/pCUP2-PlacUV5-phaC$_{Re}$ strain produced in Production Example 12 was used. The 3HH monomer proportion in the resultant PHA mixture was 3.7% by mole. Furthermore, about the resultant PHA mixture, the PHA blend ratio was analyzed, an evaluation was made by the annealing method, and the solidification period was measured. The obtained results are shown in Table 3. A DSC curve of the resultant PHA mixture is shown in FIG. 6, and a DSC curve of a product obtained by annealing the mixture by the annealing method is shown in FIG. 7.

Example 11

Production of PHA Mixture, Using KNK-005ΔphaZ1::Plac-phaC$_{Re}$ΔphaZ2,6 Strain

A PHA mixture was produced in the same way as in Example 6 except that instead of the KNK-005 REP-phaJ4bΔphaZ1::Plac-phaC$_{Re}$ΔphaZ2,6 strain, the KNK-005ΔphaZ1::Plac-phaC$_{Re}$ΔphaZ2,6 strain produced in Production Example 13 was used. The 3HH monomer proportion in the resultant PHA mixture was 4.1% by mole. Furthermore, about the resultant PHA mixture, the PHA blend ratio was analyzed, an evaluation was made by the annealing method, and the solidification period was measured. The obtained results are shown in Table 3.

Comparative Example 2

Production of PHA, Using KNK-005ΔphaZ1,2,6 Strain

A PHA was produced in the same way as in Example 1 except that instead of the KNK-005 REP-phaJ4bΔphaZ1,2,6/pCUP2-Plac-phaC$_{Re}$ strain, the KNK-005ΔphaZ1,2,6 strain produced in Production Example 1 was used. The 3HH monomer proportion in the resultant PHA, that is, PHBH was 4.8% by mole. Furthermore, about the resultant PHA, the PHA blend ratio was analyzed, an evaluation was made by the annealing method, and the solidification period was measured. The obtained results are shown in Table 3. A DSC curve of the resultant PHA is shown in FIG. 8.

TABLE 3

| | Bacterial strain name | Melting calorie in region of temperature points higher than 160° C. (J/g) | Presumed PHB content (wt %) | Higher-temperature-point calorie after annealing (J/g) | Solidification period (seconds) |
|---|---|---|---|---|---|
| Example 11 | KNK-005 Δ phaZ1::Plac-pha C$_{Re}$ Δ phaZ2,6 | 1.01 | 8.0 | 6.17 | 24 |
| Example 9 | KNK-005 Δ phaZ1,2,6/ pCUP2-REP-phaC$_{Re}$ | 3.42 | 11.7 | 13.8 | 26 |
| Example 10 | KNK-005 Δ phaZ1,2,6/ pCUP2-PlacUV5-phaC$_{Re}$ | 5.88 | 14.6 | 22.8 | 13 |
| Comparative Example 2 | KNK-005 Δ phaZ1,2,6 | — | 0 | — | 65 |

From the results in Table 3, it has been understood that according to the co-production of a PHBH and a PHB, a melting calorie is generated at temperature points higher than 160° C. so that the crystallization/solidification speed of the polymers is largely improved. It has been verified that the 3HH monomer proportion in the PHBH in the PHA mixture obtained in each of Examples 9 to 11 is from about 4 to 6% by mole from the 3HH monomer proportion and the presumed PHB content in the PHA mixture.

The invention claimed is:

1. A method for producing a mixture of polyhydroxyalkanoic acid (PHA) polymers comprising hydroxyalkanoic acid monomeric units, the method comprising:
   culturing a microorganism comprising two different genes encoding two different PHA synthases that synthesize two different PHA polymers,
   wherein a first gene of the two different genes encodes a first PHA synthase that synthesizes a first PHA polymer, a PHA copolymer (A), which is derived from the genus *Aeromonas*, and a second gene of the two different genes encodes a second PHA synthase that synthesizes a second PHA polymer, a PHA polymer (B), that has a melting point different from a melting point of the PHA copolymer (A) by at least 10° C., such that the PHA copolymer (A) and the PHA polymer (B) are independently and simultaneously produced in a cell of the microorganism, thereby producing the mixture of the PHA copolymer (A) and the PHA polymer (B) in the cell,
   wherein the melting point of the PHA polymer (B) is higher than the melting point of the PHA copolymer (A), and the PHA polymer (B) is a polymer comprising at least 99% by mole of 3-hydroxybutyric acid as a monomeric unit,
   wherein the PHA copolymer (A) is a copolymer comprising 3-hydroxybutyric acid and 3-hydroxyhexanoic acid as monomer units,
   wherein the PHA copolymer (A) comprises at least 8% by mole of the 3-hydroxyhexanoic acid as a monomeric unit,
   wherein an amount of the PHA polymer (B) in the mixture is from 0.1 to 20 wt. % based on the total amount of the PHA copolymer (A) and the PHA polymer (B), and
   wherein the mixture of the produced PHA polymers has a plurality of endothermic peaks between 85° C. and 180° C. in a differential scanning calorimetry (DSC) curve of the mixture, and, among the endothermic peaks, an endothermic peak at a highest temperature has a calorie of 0.2 to 20 J/g.

2. The method according to claim 1, wherein the second gene is a gene encoding a PHA synthase derived from a biological species different from the genus *Aeromonas*.

3. The method according to claim 1, wherein the PHA polymer (B) is a polyhydoxybutyrate homopolymer.

4. The method according to claim 1, wherein the second gene is a gene encoding a PHA synthase derived from the genus *Acinetobacter, Aeromonas, Alcaligenes, Allochromatium, Azorhizobium, Azotobacter, Bacillus, Burkholderia, Caulobacter, Chromobacterium, Comamonas, Cupriavidus, Ectothiorhodospira, Klebsiella, Methylobacterium, Paracoccus, Pseudomonas, Ralstonia, Rhizobium, Rhodobacter, Rhodococcus, Rhodospirillum, Rickettsia, Sinorhizobium, Sphingomonas, Synechocystis, Thiococcus, Thiocystis, Vibrio, Wautersia,* or *Zoogloea*.

5. The method according to claim 1, wherein the second gene is a gene encoding a PHA synthase derived from the genus *Acinetobacter, Alcaligenes, Allochromatium, Azorhizobium, Azotobacter, Bacillus, Burkholderia, Caulobacter, Chromobacterium, Comamonas, Cupriavidus, Ectothiorhodospira, Klebsiella, Methylobacterium, Paracoccus, Pseudomonas, Ralstonia, Rhizobium, Rhodobacter, Rhodococcus, Rhodospirillum, Rickettsia, Sinorhizobium, Sphingomonas, Synechocystis, Thiococcus, Thiocystis, Vibrio, Wautersia,* or *Zoogloea*.

6. The method according to claim 1, wherein the second gene is a gene encoding a PHA synthase derived from the genus *Cupriavidus*.

7. The method according to claim 1, wherein the second gene is a gene encoding a PHA synthase derived from *Cupriavidus necator*.

8. The method according to claim 1, wherein the PHA copolymer (A) has a melting point of 130° C. or lower.

9. The method according to claim 1, wherein the amount of the PHA polymer (B) in the mixture is from 0.5 to 15 wt. % based on the total amount of the PHA copolymer (A) and the PHA polymer (B).

10. The method according to claim 1, wherein the amount of the PHA polymer (B) in the mixture is from 1 to 12 wt. % based on the total amount of the PHA copolymer (A) and the PHA polymer (B).

11. The method according to claim 1, wherein the amount of the PHA polymer (B) in the mixture is from 1.2 to 9 wt. % based on the total amount of the PHA copolymer (A) and the PHA polymer (B).

12. The method according to claim 1, wherein the amount of the PHA polymer (B) in the mixture is from 2 to 7 wt. % based on the total amount of the PHA copolymer (A) and the PHA polymer (B).

* * * * *

SEQUENCE LISTING

<160> NUMBER OF SEQ ID NOS: 67

<210> SEQ ID NO 1
<211> LENGTH: 594
<212> TYPE: PRT
<213> ORGANISM: Aeromonas caviae

<400> SEQUENCE: 1

```
Met Ser Gln Pro Ser Tyr Gly Pro Leu Phe Glu Ala Leu Ala His Tyr
1               5                   10                  15

Asn Asp Lys Leu Leu Ala Met Ala Lys Ala Gln Thr Glu Arg Thr Ala
            20                  25                  30

Gln Ala Leu Leu Gln Thr Asn Leu Asp Asp Leu Gly Gln Val Leu Glu
        35                  40                  45

Gln Gly Ser Gln Gln Pro Trp Gln Leu Ile Gln Ala Gln Met Asn Trp
    50                  55                  60

Trp Gln Asp Gln Leu Lys Leu Met Gln His Thr Leu Leu Lys Ser Ala
65                  70                  75                  80

Gly Gln Pro Ser Glu Pro Val Ile Thr Pro Glu Arg Ser Asp Arg Arg
                85                  90                  95

Phe Lys Ala Glu Ala Trp Ser Glu Gln Pro Ile Tyr Asp Tyr Leu Lys
            100                 105                 110

Gln Ser Tyr Leu Leu Thr Ala Arg His Leu Leu Ala Ser Val Asp Ala
        115                 120                 125

Leu Glu Gly Val Pro Gln Lys Ser Arg Glu Arg Leu Arg Phe Phe Thr
    130                 135                 140

Arg Gln Tyr Val Asn Ala Met Ala Pro Ser Asn Phe Leu Ala Thr Asn
145                 150                 155                 160

Pro Glu Leu Leu Lys Leu Thr Leu Glu Ser Asp Gly Gln Asn Leu Val
                165                 170                 175

Arg Gly Leu Ala Leu Leu Ala Glu Asp Leu Glu Arg Ser Ala Asp Gln
            180                 185                 190

Leu Asn Ile Arg Leu Thr Asp Glu Ser Ala Phe Glu Leu Gly Arg Asp
        195                 200                 205

Leu Ala Leu Thr Pro Gly Arg Val Val Gln Arg Thr Glu Leu Tyr Glu
    210                 215                 220

Leu Ile Gln Tyr Ser Pro Thr Thr Glu Thr Val Gly Lys Thr Pro Val
225                 230                 235                 240

Leu Ile Val Pro Pro Phe Ile Asn Lys Tyr Tyr Ile Met Asp Met Arg
                245                 250                 255

Pro Gln Asn Ser Leu Val Ala Trp Leu Val Ala Gln Gly Gln Thr Val
            260                 265                 270

Phe Met Ile Ser Trp Arg Asn Pro Gly Val Ala Gln Ala Gln Ile Asp
        275                 280                 285

Leu Asp Asp Tyr Val Val Asp Gly Val Ile Ala Ala Leu Asp Gly Val
    290                 295                 300

Glu Ala Ala Thr Gly Glu Arg Glu Val His Gly Ile Gly Tyr Cys Ile
305                 310                 315                 320

Gly Gly Thr Ala Leu Ser Leu Ala Met Gly Trp Leu Ala Ala Arg Arg
                325                 330                 335

Gln Lys Gln Arg Val Arg Thr Ala Thr Leu Phe Thr Thr Leu Leu Asp
            340                 345                 350

Phe Ser Gln Pro Gly Glu Leu Gly Ile Phe Ile His Glu Pro Ile Ile
        355                 360                 365
```

Ala Ala Leu Glu Ala Gln Asn Glu Ala Lys Gly Ile Met Asp Gly Arg
370                 375                 380

Gln Leu Ala Val Ser Phe Ser Leu Leu Arg Glu Asn Ser Leu Tyr Trp
385                 390                 395                 400

Asn Tyr Tyr Ile Asp Ser Tyr Leu Lys Gly Gln Ser Pro Val Ala Phe
            405                 410                 415

Asp Leu Leu His Trp Asn Ser Asp Ser Thr Asn Val Ala Gly Lys Thr
            420                 425                 430

His Asn Ser Leu Leu Arg Arg Leu Tyr Leu Glu Asn Gln Leu Val Lys
        435                 440                 445

Gly Glu Leu Lys Ile Arg Asn Thr Arg Ile Asp Leu Gly Lys Val Lys
    450                 455                 460

Thr Pro Val Leu Leu Val Ser Ala Val Asp Asp His Ile Ala Leu Trp
465                 470                 475                 480

Gln Gly Thr Trp Gln Gly Met Lys Leu Phe Gly Gly Glu Gln Arg Phe
                485                 490                 495

Leu Leu Ala Glu Ser Gly His Ile Ala Gly Ile Ile Asn Pro Pro Ala
                500                 505                 510

Ala Asn Lys Tyr Gly Phe Trp His Asn Gly Ala Glu Ala Glu Ser Pro
            515                 520                 525

Glu Ser Trp Leu Ala Gly Ala Thr His Gln Gly Gly Ser Trp Trp Pro
530                 535                 540

Glu Met Met Gly Phe Ile Gln Asn Arg Asp Glu Gly Ser Glu Pro Val
545                 550                 555                 560

Pro Ala Arg Val Pro Glu Glu Gly Leu Ala Pro Ala Pro Gly His Tyr
                565                 570                 575

Val Lys Val Arg Leu Asn Pro Val Phe Ala Cys Pro Thr Glu Glu Asp
            580                 585                 590

Ala Ala

<210> SEQ ID NO 2
<211> LENGTH: 1785
<212> TYPE: DNA
<213> ORGANISM: Aeromonas caviae

<400> SEQUENCE: 2
atgagccaac catcttatgg cccgctgttc gaggccctgg cccactacaa tgacaagctg      60
ctggccatgg ccaaggccca gacagagcgc accgcccagg cgctgctgca gaccaatctg     120
gacgatctgg ccaggtgct ggagcaggc agccagcaac cctggcagct gatccaggcc     180
cagatgaact ggtggcagga tcagctcaag ctgatgcagc acaccctgct caaaagcgca     240
ggccagccga cgagccggt gatcaccccg gagcgcagcg atcgccgctt caaggccgag     300
gcctggagcg aacaacccat ctatgactac ctcaagcagt cctacctgct caccgccagg     360
cacctgctgg cctcggtgga tgccctggag gcgtccccc agaagagccg ggagcggctg     420
cgtttcttca cccgccagta cgtcaacgcc atggccccca gcaacttcct ggccaccaac     480
cccgagctgc tcaagctgac cctggagtcc gacggccaga acctggtgcg cggactggcc     540
ctcttggccg aggatctgga gcgcagcgcc gatcagctca catccgcct gaccgacgaa     600 tccgccttcg agctcgggcg ggatctggcc ctgaccccgg ccgggtggt gcagcgcacc     660 gagctctatg agctcattca gtacagcccg actaccgaga cggtgggcaa gacctgtg     720 ctgatagtgc cgcccttcat caacaagtac tacatcatgg acatgcggcc ccagaactcc     780
ctggtcgcct ggctggtcgc ccagggccag acggtattca tgatctcctg cgcaacccg     840

```
ggcgtggccc aggcccaaat cgatctcgac gactacgtgg tggatggcgt catcgccgcc    900
ctggacggcg tggaggcggc caccggcgag cgggaggtgc acggcatcgg ctactgcatc    960
ggcggcaccg ccctgtcgct cgccatgggc tggctggcgg cgcggcgcca gaagcagcgg    1020
gtgcgcaccg ccaccctgtt cactaccctg ctggacttct cccagcccgg ggagcttggc    1080
atcttcatcc acgagcccat catagcggcg ctcgaggcgc aaaatgaggc caagggcatc    1140
atggacgggc gccagctggc ggtctccttc agcctgctgc gggagaacag cctctactgg    1200
aactactaca tcgacagcta cctcaagggt cagagcccgg tggccttcga tctgctgcac    1260
tggaacagcg acagcaccaa tgtggcgggc aagacccaca cagcctgct gcgccgtctc    1320 tacctggaga accagctggt gaaggggag ctcaagatcc gcaacacccg catcgatctc    1380
ggcaaggtga agacccctgt gctgctggtg tcggcggtgg acgatcacat cgccctctgg    1440
cagggcacct ggcagggcat gaagctgttt ggcggggagc agcgcttcct cctggcggag    1500
tccggccaca tcgccggcat catcaacccg ccggccgcca acaagtacgg cttctggcac    1560
aacggggccg aggccgagag cccggagagc tggctggcag gggcgacgca ccagggcggc    1620
tcctggtggc ccgagatgat gggctttatc cagaaccgtg acgaagggtc agagcccgtc    1680
cccgcgcggg tcccggagga agggctggcc ccgcccccg gccactatgt caaggtgcgg    1740
ctcaaccccg tgtttgcctg cccaacagag gaggacgccg catga                    1785

<210> SEQ ID NO 3
<211> LENGTH: 1785
<212> TYPE: DNA
<213> ORGANISM: Artificial Sequence
<220> FEATURE:
<223> OTHER INFORMATION: Artificially mutated gene derived from
      Aeromonas caviae

<400> SEQUENCE: 3
atgagccaac catcttatgg cccgctgttc gaggccctgg cccactacaa tgacaagctg     60
ctggccatgg ccaaggccca gacagagcgc accgcccagg cgctgctgca gaccaatctg    120
gacgatctgg ccaggtgct ggagcagggc agccagcaac cctggcagct gatccaggcc     180
cagatgaact ggtggcagga tcagctcaag ctgatgcagc acaccctgct caaaagcgca    240
ggccagccga gcgagccggt gatcaccccg gagcgcagcg atcgccgctt caaggccgag    300
gcctggagcg aacaacccat ctatgactac ctcaagcagt cctacctgct caccgccagg    360
cacctgctgg cctcggtgga tgccctggag gcgtcccc agaagagccg ggagcggctg     420
cgtttcttca cccgccagta cgtcagcgcc atggccccca gcaacttcct ggccaccaac    480
cccgagctgc tcaagctgac cctggagtcc ggcggccaga acctggtgcg cggactggcc    540
ctcttggccg aggatctgga gcgcagcgcc gatcagctca acatccgcct gaccgacgaa    600
tccgccttcg agctcgggcg ggatctggcc ctgaccccgg ccgggtggt gcagcgcacc    660 gagctctatg agctcattca gtacagcccg actaccgaga cggtgggcaa gacacctgtg    720
ctgatagtgc cgcccttcat caacaagtac tacatcatgg acatgcggcc ccagaactcc    780
ctggtcgcct ggctggtcgc ccagggccag acggtattca tgatctcctg gcgcaacccg    840
ggcgtggccc aggcccaaat cgatctcgac gactacgtgg tggatggcgt catcgccgcc    900
ctggacggcg tggaggcggc caccggcgag cgggaggtgc acggcatcgg ctactgcatc    960
ggcggcaccg ccctgtcgct cgccatgggc tggctggcgg cgcggcgcca gaagcagcgg   1020
gtgcgcaccg ccaccctgtt cactaccctg ctggacttct cccagcccgg ggagcttggc   1080
```

-continued

```
atcttcatcc acgagcccat catagcggcg ctcgaggcgc aaaatgaggc caagggcatc    1140
atggacgggc gccagctggc ggtctccttc agcctgctgc gggagaacag cctctactgg    1200
aactactaca tcgacagcta cctcaagggt cagagcccgg tggccttcga tctgctgcac    1260
tggaacagcg acagcaccaa tgtggcgggc aagacccaca acagcctgct gcgccgtctc    1320
tacctggaga accagctggt gaaggggag ctcaagatcc gcaacaccg catcgatctc     1380 ggcaaggtga agacccctgt gctgctggtg tcggcggtgg acgatcacat cgccctctgg    1440
cagggcacct ggcagggcat gaagctgttt ggcggggagc agcgcttcct cctggcggag    1500
tccggccaca tcgccggcat catcaacccg ccggccgcca acaagtacgg cttctggcac    1560 aacgggccg aggccgagag cccggagagc tggctggcag gggcgacgca ccagggcggc    1620
tcctggtggc ccgagatgat gggctttatc cagaaccgtg acgaagggtc agagcccgtc    1680
cccgcgcggg tcccggagga agggctggcc cccgcccccg gccactatgt caaggtgcgg    1740
ctcaaccccg tgtttgcctg cccaacagag gaggacgccg catga                    1785

<210> SEQ ID NO 4
<211> LENGTH: 589
<212> TYPE: PRT
<213> ORGANISM: Cupriavidus necator

<400> SEQUENCE: 4

Met Ala Thr Gly Lys Gly Ala Ala Ala Ser Thr Gln Glu Gly Lys Ser
1               5                   10                  15

Gln Pro Phe Lys Val Thr Pro Gly Pro Phe Asp Pro Ala Thr Trp Leu
            20                  25                  30

Glu Trp Ser Arg Gln Trp Gln Gly Thr Glu Gly Asn Gly His Ala Ala
        35                  40                  45

Ala Ser Gly Ile Pro Gly Leu Asp Ala Leu Ala Gly Val Lys Ile Ala
    50                  55                  60

Pro Ala Gln Leu Gly Asp Ile Gln Gln Arg Tyr Met Lys Asp Phe Ser
65                  70                  75                  80

Ala Leu Trp Gln Ala Met Ala Glu Gly Lys Ala Glu Ala Thr Gly Pro
                85                  90                  95

Leu His Asp Arg Arg Phe Ala Gly Asp Ala Trp Arg Thr Asn Leu Pro
            100                 105                 110

Tyr Arg Phe Ala Ala Ala Phe Tyr Leu Leu Asn Ala Arg Ala Leu Thr
        115                 120                 125

Glu Leu Ala Asp Ala Val Glu Ala Asp Ala Lys Thr Arg Gln Arg Ile
    130                 135                 140

Arg Phe Ala Ile Ser Gln Trp Val Asp Ala Met Ser Pro Ala Asn Phe
145                 150                 155                 160

Leu Ala Thr Asn Pro Glu Ala Gln Arg Leu Leu Ile Glu Ser Gly Gly
                165                 170                 175

Glu Ser Leu Arg Ala Gly Val Arg Asn Met Met Glu Asp Leu Thr Arg
            180                 185                 190

Gly Lys Ile Ser Gln Thr Asp Glu Ser Ala Phe Glu Val Gly Arg Asn
        195                 200                 205

Val Ala Val Thr Glu Gly Ala Val Val Phe Glu Asn Glu Tyr Phe Gln
    210                 215                 220

Leu Leu Gln Tyr Lys Pro Leu Thr Asp Lys Val His Ala Arg Pro Leu
225                 230                 235                 240

Leu Met Val Pro Pro Cys Ile Asn Lys Tyr Tyr Ile Leu Asp Leu Gln
```

```
                    245                 250                 255
Pro Glu Ser Ser Leu Val Arg His Val Val Glu Gln Gly His Thr Val
            260                 265                 270

Phe Leu Val Ser Trp Arg Asn Pro Asp Ala Ser Met Ala Gly Ser Thr
            275                 280                 285

Trp Asp Asp Tyr Ile Glu His Ala Ala Ile Arg Ala Ile Glu Val Ala
            290                 295                 300

Arg Asp Ile Ser Gly Gln Asp Lys Ile Asn Val Leu Gly Phe Cys Val
305                 310                 315                 320

Gly Gly Thr Ile Val Ser Thr Ala Leu Ala Val Leu Ala Ala Arg Gly
                325                 330                 335

Glu His Pro Ala Ala Ser Val Thr Leu Leu Thr Thr Leu Leu Asp Phe
            340                 345                 350

Ala Asp Thr Gly Ile Leu Asp Val Phe Val Asp Glu Gly His Val Gln
            355                 360                 365

Leu Arg Glu Ala Thr Leu Gly Gly Ala Gly Ala Pro Cys Ala Leu
            370                 375                 380

Leu Arg Gly Leu Glu Leu Ala Asn Thr Phe Ser Phe Leu Arg Pro Asn
385                 390                 395                 400

Asp Leu Val Trp Asn Tyr Val Val Asp Asn Tyr Leu Lys Gly Asn Thr
                405                 410                 415

Pro Val Pro Phe Asp Leu Leu Phe Trp Asn Gly Asp Ala Thr Asn Leu
            420                 425                 430

Pro Gly Pro Trp Tyr Cys Trp Tyr Leu Arg His Thr Tyr Leu Gln Asn
            435                 440                 445

Glu Leu Lys Val Pro Gly Lys Leu Thr Val Cys Gly Val Pro Val Asp
        450                 455                 460

Leu Ala Ser Ile Asp Val Pro Thr Tyr Ile Tyr Gly Ser Arg Glu Asp
465                 470                 475                 480

His Ile Val Pro Trp Thr Ala Ala Tyr Ala Ser Thr Ala Leu Leu Ala
                485                 490                 495

Asn Lys Leu Arg Phe Val Leu Gly Ala Ser Gly His Ile Ala Gly Val
            500                 505                 510

Ile Asn Pro Pro Ala Lys Asn Lys Arg Ser His Trp Thr Asn Asp Ala
        515                 520                 525

Leu Pro Glu Ser Pro Gln Gln Trp Leu Ala Gly Ala Ile Glu His His
        530                 535                 540

Gly Ser Trp Trp Pro Asp Trp Thr Ala Trp Leu Ala Gly Gln Ala Gly
545                 550                 555                 560

Ala Lys Arg Ala Ala Pro Ala Asn Tyr Gly Asn Ala Arg Tyr Arg Ala
                565                 570                 575

Ile Glu Pro Ala Pro Gly Arg Tyr Val Lys Ala Lys Ala
            580                 585

<210> SEQ ID NO 5
<211> LENGTH: 1770
<212> TYPE: DNA
<213> ORGANISM: Cupriavidus necator

<400> SEQUENCE: 5
atggcgaccg gcaaaggcgc ggcagcttcc acgcaggaag gcaagtccca accattcaag      60
gtcacgccgg ggccattcga tccagccaca tggctggaat ggtcccgcca gtggcagggc     120
actgaaggca acggccacgc ggccgcgtcc ggcattccgg gcctggatgc gctggcaggc     180
```

-continued

```
gtcaagatcg cgccggcgca gctgggtgat atccagcagc gctacatgaa ggacttctca    240
gcgctgtggc aggccatggc cgagggcaag gccgaggcca ccgtccgct gcacgaccgg     300
cgcttcgccg gcgacgcatg gcgcaccaac ctcccatatc gcttcgctgc cgcgttctac   360
ctgctcaatg cgcgcgcctt gaccgagctg gccgatgccg tcgaggccga tgccaagacc    420
cgccagcgca tccgcttcgc gatctcgcaa tgggtcgatg cgatgtcgcc cgccaacttc    480
cttgccacca atcccgaggc gcagcgcctg ctgatcgagt cgggcggcga atcgctgcgt    540
gccggcgtgc gcaacatgat ggaagacctg acacgcggca agatctcgca gaccgacgag   600
agcgcgtttg aggtcggccg caatgtcgcg gtgaccgaag cgccgtggt cttcgagaac     660
gagtacttcc agctgttgca gtacaagccg ctgaccgaca aggtgcacgc gcgcccgctg    720
ctgatggtgc cgccgtgcat caacaagtac tacatcctgg acctgcagcc ggagagctcg    780
ctggtgcgcc atgtggtgga gcagggacat acggtgtttc tggtgtcgtg gcgcaatccg    840
gacgccagca tggccggcag cacctgggac gactacatcg agcacgcggc catccgcgcc    900
atcgaagtcg cgcgcgacat cagcggccag gacaagatca acgtgctcgg cttctgcgtg    960
ggcggcacca ttgtctcgac cgcgctggcg gtgctggccg cgcgcggcga gcacccggcc   1020
gccagcgtca cgctgctgac cacgctgctg gactttgccg acacgggcat cctcgacgtc   1080
tttgtcgacg agggccatgt gcagttgcgc gaggccacgc tgggcggcgg cgccggcgcg   1140
ccgtgcgcgc tgctgcgcgg ccttgagctg gccaatacct tctcgttctt gcgcccgaac   1200
gacctggtgt ggaactacgt ggtcgacaac tacctgaagg gcaacacgcc ggtgccgttc   1260
gacctgctgt tctggaacgg cgacgccacc aacctgccgg ggccgtggta ctgctggtac   1320
ctgcgccaca cctacctgca gaacgagctc aaggtaccgg gcaagctgac cgtgtgcggc   1380
gtgccggtgg acctggccag catcgacgtg ccgacctata tctacggctc gcgcgaagac   1440
catatcgtgc cgtggaccgc ggcctatgcc tcgaccgcgc tgctggcgaa caagctgcgc   1500
ttcgtgctgg gtgcgtcggg ccatatcgcc ggtgtgatca cccgccggc caagaacaag    1560
cgcagccact ggactaacga tgcgctgccg gagtcgccgc agcaatggct ggccggcgcc   1620
atcgagcatc acggcagctg gtggccggac tggaccgcat ggctgccgg gcaggccggc    1680
gcgaaacgcg ccgcgcccgc caactatggc aatgcgcgct atcgcgcaat cgaacccgcg   1740
cctgggcgat acgtcaaagc caaggcatga                                    1770
```

<210> SEQ ID NO 6
<211> LENGTH: 123
<212> TYPE: DNA
<213> ORGANISM: Escherichia coli

<400> SEQUENCE: 6

```
gcgcaacgca attaatgtga gttagctcac tcattaggca ccccaggctt tacactttat    60
gcttccggct cgtatgttgt gtggaattgt gagcggataa caatttcaca caggaaacaa   120
ttg                                                                 123
```

<210> SEQ ID NO 7
<211> LENGTH: 232
<212> TYPE: DNA
<213> ORGANISM: Escherichia coli

<400> SEQUENCE: 7

```
tgcttctggc gtcaggcagc catcggaagc tgtggtatgg ctgtgcaggt cgtaaatcac    60
tgcataattc gtgtcgctca aggcgcactc ccgttctgga taatgttttt tgcgccgaca   120
```

```
tcataacggt tctggcaaat attctgaaat gagctgttga caattaatca tcgaactagt    180
taactagtac gcaagttcac agcggataac aatttcacac aggaaacaat tg            232

<210> SEQ ID NO 8
<211> LENGTH: 123
<212> TYPE: DNA
<213> ORGANISM: Artificial Sequence
<220> FEATURE:
<223> OTHER INFORMATION: Artificially mutated promoter derived from
      Escherichia coli

<400> SEQUENCE: 8
gcgcaacgca attaatgtga gttagctcac tcattaggca ccccaggctt tacactttat    60
gcttccggct cgtataatgt gtggaattgt gagcggataa caatttcaca caggaaacaa   120
ttg                                                                 123

<210> SEQ ID NO 9
<211> LENGTH: 235
<212> TYPE: DNA
<213> ORGANISM: Artificial Sequence
<220> FEATURE:
<223> OTHER INFORMATION: artificial promoter

<400> SEQUENCE: 9
caattgtgct tctggcgtca ggcagccatc ggaagctgtg gtatggctgt gcaggtcgta    60
aatcactgca taattcgtgt cgctcaaggc gcactcccgt tctggataat gttttttgcg   120
ccgacatcat aacggttctg gcaaatattc tgaaatgagc tgttgacaat taatcatcgg   180
ctcgtataat gtgtggaatt gtgagcggat aacaatttca caggaaac aattg          235

<210> SEQ ID NO 10
<211> LENGTH: 236
<212> TYPE: DNA
<213> ORGANISM: Artificial Sequence
<220> FEATURE:
<223> OTHER INFORMATION: artificial promoter

<400> SEQUENCE: 10
caattgtgct tctggcgtca ggcagccatc ggaagctgtg gtatggctgt gcaggtcgta    60
aatcactgca taattcgtgt cgctcaaggc gcactcccgt tctggataat gttttttgcg   120
ccgacatcat aacggttctg gcaaatattc tgaaatgagc tgttgacaat taatcatcga   180
actagtttaa tgtgtggaat tgtgagcgga taacaatttc acaggaaa caattg         236

<210> SEQ ID NO 11
<211> LENGTH: 237
<212> TYPE: DNA
<213> ORGANISM: Artificial Sequence
<220> FEATURE:
<223> OTHER INFORMATION: artificial promoter

<400> SEQUENCE: 11
caattgtgct tctggcgtca ggcagccatc ggaagctgtg gtatggctgt gcaggtcgta    60
aatcactgca taattcgtgt cgctcaaggc gcactcccgt tctggataat gttttttgcg   120
ccgacatcat aacggttctg gcaaatattc tgaaatgagc tgttgacaat taatcatcgc   180
ggctcgtata atgtgtggaa ttgtgagcgg ataacaattt cacacaggaa acaattg      237

<210> SEQ ID NO 12
<211> LENGTH: 236
```

<212> TYPE: DNA
<213> ORGANISM: Artificial Sequence
<220> FEATURE:
<223> OTHER INFORMATION: artificial promoter

<400> SEQUENCE: 12

| | | | | | |
|---|---|---|---|---|---|
| caattgtgct | tctggcgtca | ggcagccatc | ggaagctgtg | gtatggctgt | gcaggtcgta | 60 |
| aatcactgca | taattcgtgt | cgctcaaggc | gcactcccgt | tctggataat | gttttttgcg | 120 |
| ccgacatcat | aacggttctg | gcaaatattc | tgaaatgagc | tgttgacaat | taatcatccg | 180 |
| gctcgtataa | tgtgtggaat | tgtgagcgga | taacaatttc | acacaggaaa | caattg | 236 |

<210> SEQ ID NO 13
<211> LENGTH: 818
<212> TYPE: DNA
<213> ORGANISM: Cupriavidus necator

<400> SEQUENCE: 13

| | | | | | |
|---|---|---|---|---|---|
| cccgggcaag | taccttgccg | acatctatgc | gctggcgcgc | acgcgcctgg | cgcgcgccgg | 60 |
| ctgtaccgag | gtctacggcg | gcgacgcctg | caccgtggcc | gacgccggtc | gcttctactc | 120 |
| ctatcggcgc | gatggcgtga | ccggccgcat | ggccagcctg | gtctggctgg | cggactgagc | 180 |
| ccgccgctgc | ctcactcgtc | cttgcccctg | gccgcctgcg | cgcgctcggc | ttcagccttg | 240 |
| cgtcggcggc | ggccgggcgt | gcccatgatg | tagagcacca | cgccaccgg | cgccatgcca | 300 |
| tacatcagga | aggtggcaac | gcctgccacc | acgttgtgct | cggtgatcgc | catcatcagc | 360 |
| gccacgtaga | gccagccaat | ggccacgatg | tacatcaaaa | attcatcctt | ctcgcctatg | 420 |
| ctctggggcc | tcggcagatg | cgagcgctgc | ataccgtccg | gtaggtcggg | aagcgtgcag | 480 |
| tgccgaggcg | gattcccgca | ttgacagcgc | gtgcgttgca | aggcaacaat | ggactcaaat | 540 |
| gtctcggaat | cgctgacgat | tcccaggttt | ctccggcaag | catagcgcat | ggcgtctcca | 600 |
| tgcgagaatg | tcgcgcttgc | cggataaaag | gggagccgct | atcggaatgg | acgcaagcca | 660 |
| cggccgcagc | aggtgcggtc | gagggcttcc | agccagttcc | agggcagatg | tgccggcaga | 720 |
| ccctcccgct | ttgggggagg | cgcaagccgg | gtccattcgg | atagcatctc | cccatgcaaa | 780 |
| gtgccggcca | gggcaatgcc | cggagccggt | tcgaatag | | | 818 |

<210> SEQ ID NO 14
<211> LENGTH: 817
<212> TYPE: DNA
<213> ORGANISM: Artificial Sequence
<220> FEATURE:
<223> OTHER INFORMATION: Artificially mutated promoter derived from Cupriavidus necator

<400> SEQUENCE: 14

| | | | | | |
|---|---|---|---|---|---|
| cccgggcaag | taccttgccg | acatctatgc | gctggcgcgc | acgcgcctgg | cgcgcgccgg | 60 |
| ctgtaccgag | gtctacggcg | gcgacgcctg | caccgtggcc | gacgccggtc | gcttctactc | 120 |
| ctatcggcgc | gatggcgtga | ccggccgcat | ggccagcctg | gtctggctgg | cggactgagc | 180 |
| ccgccgctgc | ctcactcgtc | cttgcccctg | gccgcctgcg | cgcgctcggc | ttcagccttg | 240 |
| cgtcggcggc | ggccgggcgt | gcccatgatg | tagagcacca | cgccaccgg | cgccatgcca | 300 |
| tacatcagga | aggtggcaac | gcctgccacc | acgttgtgct | cggtgatcgc | catcatcagc | 360 |
| gccacgtaga | gccagccaat | ggccacgatg | tacatcaaaa | attcatcctt | ctcgcctatg | 420 |
| ctctggggcc | tcggcagatg | cgagcgctgc | ataccgtccg | gtaggtcggg | aagcgtgcag | 480 |
| tgccgaggcg | gattcccgca | ttgacagcgc | gtgcttgcaa | ggcaacaatg | gactcaaatg | 540 |

```
tctcggaatc gctgacgatt cccaggtttc tccggcaagc atagcgcatg gcgtctccat    600
gcgagaatgt cgcgcttgcc ggataaaagg ggagccgcta tcggaatgga cgcaagccac    660
ggccgcagca ggtgcggtcg agggcttcca gccagttcca gggcagatgt gccggcagac    720
cctcccgctt tggggaggc gcaagccggg tccattcgga tagcatctcc ccatgcaaag    780
tgccggccag ggcaatgccc ggagccggtt cgaatag                              817

<210> SEQ ID NO 15
<211> LENGTH: 268
<212> TYPE: DNA
<213> ORGANISM: Cupriavidus necator

<400> SEQUENCE: 15
catggccctc gccggagcgc cccggagtgg cgtcacagcc gctcccgtgt atcgccagca     60
acgttgtttg tgcattgcac aaaatccact tgacattgga tctggcgccc ctaaaatagg    120
aattgttgcg gcgcaccaaa taagaaatgc gccttgaccc acccacacgc tgggctggc    180 cgaatcgggc acaacaccgt cacggccctg acatctaggc ggcttaattt gctagacctt    240
gaagttcacc actggagacc agcaattg                                        268

<210> SEQ ID NO 16
<211> LENGTH: 24
<212> TYPE: DNA
<213> ORGANISM: Cupriavidus necator

<400> SEQUENCE: 16
cacgtgcaga gagacaatca aatc                                             24

<210> SEQ ID NO 17
<211> LENGTH: 24
<212> TYPE: DNA
<213> ORGANISM: Artificial Sequence
<220> FEATURE:
<223> OTHER INFORMATION: Artificially mutated SD sequence derived from
      Cupriavidus necator

<400> SEQUENCE: 17
cacgtgctct ctctcaatca aatc                                             24

<210> SEQ ID NO 18
<211> LENGTH: 670
<212> TYPE: DNA
<213> ORGANISM: Cupriavidus necator

<400> SEQUENCE: 18
tgagtagtga gccgcgtgga ttctgcgcca tgcggttgtt cccgaacggt cgttctaaaa     60
aatttagcac gaccgttcac aaaatttcga ttcgcggata atatagcttt tgacgggctg    120
gaaagatcat gaaggtgctc gacctgcgct gcgcgcatga ccatggtttc gagggctggt    180
ttgcctcgga agaagatgcg cagtcgcaaa tctcgcgtga cctcgtccaa tgcccggtct    240
gtggcgacca cgccgtgacg cggctgccca gcgcgccgcg cctgaacctg tcgggcgcga    300
ccgcgcgcga aggcagcgcc aggccggcgc agccggctgc cgcaccggag acactgcaag    360
cgctctatat gaaggcagtg aagcaggtgc tggcacagac cgaggatgtt ggcgatcgct    420 tgccgaaga ggcaaggcgc atgcactatg acgaggcgcc ggaacgcggc attcgcggtt    480
cggcctcggc ggaggaggtg caggcgctgg ccgaagaggg catcgagact ttcccgctcg    540
tggtgccgga tgcgctgaag cagacggctc actgaattgc gtcttgtgcc cgtttgctgt    600
```

```
cggcgcttga cgtgcaggca gaacaaaccg ccggcggccc cacgccaagc cggcaccact    660
ggagacgggc                                                          670
```

<210> SEQ ID NO 19
<211> LENGTH: 385
<212> TYPE: DNA
<213> ORGANISM: Aeromonas caviae

<400> SEQUENCE: 19

```
cgatctggac cggggtgctg gcctgggcca cgccggcgag ggccagcgcg gagcaaccga     60
gcagcagggc gagaggtttc atcgggattc cttggcagtc tgaatgacgt gccagcctat    120
cagcgcggcg ccggtgcggc gagggcgcgc cggacccagt gcgtcacctc tcgtctgatc    180
cgcctccctc gacgggcgtc gctgacaaaa aaattcaaac agaaattaac atttatgtca    240
tttacaccaa accgcatttg gttgcagaat gctcaaacgt gtgtttgaac agagcaagca    300
acacgtaaac agggatgaca tgcagtaccc gtaagaaggg ccgattggcc cagatctcgc    360
ctcgggtgtg ggtgaaggag agcac                                         385
```

<210> SEQ ID NO 20
<211> LENGTH: 32
<212> TYPE: DNA
<213> ORGANISM: Artificial Sequence
<220> FEATURE:
<223> OTHER INFORMATION: primer

<400> SEQUENCE: 20

```
gcgcatttaa atccggacct tcgtgcggct ca                                  32
```

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21

```
gaggactcct gatcgtgtga                                                20
```

<210> SEQ ID NO 22
<211> LENGTH: 40
<212> TYPE: DNA
<213> ORGANISM: Artificial Sequence
<220> FEATURE:
<223> OTHER INFORMATION: primer

<400> SEQUENCE: 22

```
tcacacgatc aggagtcctc agtcgggcag caccaatgcg                          40
```

<210> SEQ ID NO 23
<211> LENGTH: 32
<212> TYPE: DNA
<213> ORGANISM: Artificial Sequence
<220> FEATURE:
<223> OTHER INFORMATION: primer

<400> SEQUENCE: 23

```
gcgcatttaa atcgccacgc tgtgcctgac ga                                  32
```

<210> SEQ ID NO 24
<211> LENGTH: 34
<212> TYPE: DNA

```
<213> ORGANISM: Artificial Sequence
<220> FEATURE:
<223> OTHER INFORMATION: primer

<400> SEQUENCE: 24
gcgcgcattt aaatcatggc atctacgccg tcgg                          34

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
gccttttctg cctgggtcta                                          20

<210> SEQ ID NO 26
<211> LENGTH: 40
<212> TYPE: DNA
<213> ORGANISM: Artificial Sequence
<220> FEATURE:
<223> OTHER INFORMATION: primer

<400> SEQUENCE: 26
tagacccagg cagaaaaggc gaaaacgccc gcgattgcgg                    40

<210> SEQ ID NO 27
<211> LENGTH: 34
<212> TYPE: DNA
<213> ORGANISM: Artificial Sequence
<220> FEATURE:
<223> OTHER INFORMATION: primer

<400> SEQUENCE: 27
gcgcgcattt aaatacgctg gcgcgtttcg tctg                          34

<210> SEQ ID NO 28
<211> LENGTH: 32
<212> TYPE: DNA
<213> ORGANISM: Artificial Sequence
<220> FEATURE:
<223> OTHER INFORMATION: primer

<400> SEQUENCE: 28
aaatagattt aaatgggaca gcagcaggat tt                            32

<210> SEQ ID NO 29
<211> LENGTH: 38
<212> TYPE: DNA
<213> ORGANISM: Artificial Sequence
<220> FEATURE:
<223> OTHER INFORMATION: primer

<400> SEQUENCE: 29
gctggcggct gccgggggct cggtccccgc tattctgg                      38

<210> SEQ ID NO 30
<211> LENGTH: 38
<212> TYPE: DNA
<213> ORGANISM: Artificial Sequence
<220> FEATURE:
<223> OTHER INFORMATION: primer

<400> SEQUENCE: 30
ccagaatagc ggggaccgag cccccggcag ccgccagc                      38
```

<210> SEQ ID NO 31
<211> LENGTH: 33
<212> TYPE: DNA
<213> ORGANISM: Artificial Sequence
<220> FEATURE:
<223> OTHER INFORMATION: primer

<400> SEQUENCE: 31
aaatagattt aaatacaaag gcaaagggt agc                          33

<210> SEQ ID NO 32
<211> LENGTH: 34
<212> TYPE: DNA
<213> ORGANISM: Artificial Sequence
<220> FEATURE:
<223> OTHER INFORMATION: primer

<400> SEQUENCE: 32
gcgcgcattt aaatgcaagc agttcggcgt ggcg                        34

<210> SEQ ID NO 33
<211> LENGTH: 25
<212> TYPE: DNA
<213> ORGANISM: Artificial Sequence
<220> FEATURE:
<223> OTHER INFORMATION: primer

<400> SEQUENCE: 33
gcttgctctt cctattcagt caggg                                  25

<210> SEQ ID NO 34
<211> LENGTH: 43
<212> TYPE: DNA
<213> ORGANISM: Artificial Sequence
<220> FEATURE:
<223> OTHER INFORMATION: primer

<400> SEQUENCE: 34
gcagagagac aatcaaatca tgaagaccta cgagaacatc gcc              43

<210> SEQ ID NO 35
<211> LENGTH: 33
<212> TYPE: DNA
<213> ORGANISM: Artificial Sequence
<220> FEATURE:
<223> OTHER INFORMATION: primer

<400> SEQUENCE: 35
gcgcgcattt aaattcaggg aaagcgccgc agg                         33

<210> SEQ ID NO 36
<211> LENGTH: 45
<212> TYPE: DNA
<213> ORGANISM: Artificial Sequence
<220> FEATURE:
<223> OTHER INFORMATION: primer

<400> SEQUENCE: 36
ccctgactga ataggaagag caagccccgg gcaagtacct tgccg             45

<210> SEQ ID NO 37
<211> LENGTH: 22
<212> TYPE: DNA
<213> ORGANISM: Artificial Sequence
<220> FEATURE:

<223> OTHER INFORMATION: primer

<400> SEQUENCE: 37
catgatttga ttgtctctct gc                                              22

<210> SEQ ID NO 38
<211> LENGTH: 32
<212> TYPE: DNA
<213> ORGANISM: Artificial Sequence
<220> FEATURE:
<223> OTHER INFORMATION: primer

<400> SEQUENCE: 38
gcgcgcgaat tccccgggca agtaccttgc cg                                   32

<210> SEQ ID NO 39
<211> LENGTH: 70
<212> TYPE: DNA
<213> ORGANISM: Artificial Sequence
<220> FEATURE:
<223> OTHER INFORMATION: primer

<400> SEQUENCE: 39
gcgcgcacta gtcggctgcc gactggttga accaggccgg caggtcaggc tcatgccttg     60
gctttgacgt                                                            70

<210> SEQ ID NO 40
<211> LENGTH: 29
<212> TYPE: DNA
<213> ORGANISM: Artificial Sequence
<220> FEATURE:
<223> OTHER INFORMATION: primer

<400> SEQUENCE: 40
gtgcaattgt gagtagtgag ccgcgtgga                                       29

<210> SEQ ID NO 41
<211> LENGTH: 20
<212> TYPE: DNA
<213> ORGANISM: Artificial Sequence
<220> FEATURE:
<223> OTHER INFORMATION: primer

<400> SEQUENCE: 41
gcccgtctcc agtggtgccg                                                 20

<210> SEQ ID NO 42
<211> LENGTH: 40
<212> TYPE: DNA
<213> ORGANISM: Artificial Sequence
<220> FEATURE:
<223> OTHER INFORMATION: primer

<400> SEQUENCE: 42
cggcaccact ggagacgggc atggcgaccg gcaaaggcgc                           40

<210> SEQ ID NO 43
<211> LENGTH: 53
<212> TYPE: DNA
<213> ORGANISM: Artificial Sequence
<220> FEATURE:
<223> OTHER INFORMATION: primer

<400> SEQUENCE: 43
gggcaattgc acgtgcagag agacaatcaa atcatgagcc aaccatctta tgg            53

```
<210> SEQ ID NO 44
<211> LENGTH: 20
<212> TYPE: DNA
<213> ORGANISM: Artificial Sequence
<220> FEATURE:
<223> OTHER INFORMATION: primer

<400> SEQUENCE: 44
gtgcaattgg cgcaacgcaa                                               20

<210> SEQ ID NO 45
<211> LENGTH: 23
<212> TYPE: DNA
<213> ORGANISM: Artificial Sequence
<220> FEATURE:
<223> OTHER INFORMATION: primer

<400> SEQUENCE: 45
gggcaattgt ttcctgtgtg aaa                                           23

<210> SEQ ID NO 46
<211> LENGTH: 38
<212> TYPE: DNA
<213> ORGANISM: Artificial Sequence
<220> FEATURE:
<223> OTHER INFORMATION: primer

<400> SEQUENCE: 46
gcgcgcattt aaatcgagga agagatcctg gcctttgc                           38

<210> SEQ ID NO 47
<211> LENGTH: 29
<212> TYPE: DNA
<213> ORGANISM: Artificial Sequence
<220> FEATURE:
<223> OTHER INFORMATION: primer

<400> SEQUENCE: 47
gtcgatagtc tcctcttgac gataaagtg                                     29

<210> SEQ ID NO 48
<211> LENGTH: 41
<212> TYPE: DNA
<213> ORGANISM: Artificial Sequence
<220> FEATURE:
<223> OTHER INFORMATION: primer

<400> SEQUENCE: 48
gcagagagac aatcaaatca tgcgtaccat cgcatcgctg g                       41

<210> SEQ ID NO 49
<211> LENGTH: 33
<212> TYPE: DNA
<213> ORGANISM: Artificial Sequence
<220> FEATURE:
<223> OTHER INFORMATION: primer

<400> SEQUENCE: 49
gcgcgcattt aaattcaccc gtagcggcgc gtg                                33

<210> SEQ ID NO 50
<211> LENGTH: 49
<212> TYPE: DNA
<213> ORGANISM: Artificial Sequence
<220> FEATURE:
```

<223> OTHER INFORMATION: primer

<400> SEQUENCE: 50
cactttatcg tcaagaggag actatcgact gcttctggcg tcaggcagc          49

<210> SEQ ID NO 51
<211> LENGTH: 106
<212> TYPE: DNA
<213> ORGANISM: Artificial Sequence
<220> FEATURE:
<223> OTHER INFORMATION: primer

<400> SEQUENCE: 51
gatttgattg tctctctgca cgtgcaattg tttcctgtgt gaaattgtta tccgctgtga          60
acttgcgtac tagttaacta gttcgatgat taattgtcaa cagctc          106

<210> SEQ ID NO 52
<211> LENGTH: 38
<212> TYPE: DNA
<213> ORGANISM: Artificial Sequence
<220> FEATURE:
<223> OTHER INFORMATION: primer

<400> SEQUENCE: 52
actagtatcg atcaattggc cttttctgcc tgggtcta          38

<210> SEQ ID NO 53
<211> LENGTH: 38
<212> TYPE: DNA
<213> ORGANISM: Artificial Sequence
<220> FEATURE:
<223> OTHER INFORMATION: primer

<400> SEQUENCE: 53
caattgatcg atactagtat tgcgggcgtt tcttcttg          38

<210> SEQ ID NO 54
<211> LENGTH: 35
<212> TYPE: DNA
<213> ORGANISM: Artificial Sequence
<220> FEATURE:
<223> OTHER INFORMATION: primer

<400> SEQUENCE: 54
gggcaattgg cgcaacgcaa ttaatgtgag ttagc          35

<210> SEQ ID NO 55
<211> LENGTH: 74
<212> TYPE: DNA
<213> ORGANISM: Artificial Sequence
<220> FEATURE:
<223> OTHER INFORMATION: primer

<400> SEQUENCE: 55
gggcaattgt ttcctgtgtg aaattgttat ccgctcacaa ttccacacat tatacgagcc          60
ggaagcataa agtg          74

<210> SEQ ID NO 56
<211> LENGTH: 120
<212> TYPE: DNA
<213> ORGANISM: Artificial Sequence
<220> FEATURE:
<223> OTHER INFORMATION: Artificially muteted promoter derived from
       Escherichia coli

<400> SEQUENCE: 56

```
gcgcaacgca attaatgtga gttagctcac tcattaggca ccccaggctt tacacatgct    60
tccggctcgt atgttgtgtg gaattgtgag cggataacaa tttcacacag gaaacaattg   120
```

<210> SEQ ID NO 57
<211> LENGTH: 121
<212> TYPE: DNA
<213> ORGANISM: Artificial Sequence
<220> FEATURE:
<223> OTHER INFORMATION: Artificially muteted promoter derived from Escherichia coli

<400> SEQUENCE: 57

```
gcgcaacgca attaatgtga gttagctcac tcattaggca ccccaggctt tacactatgc    60
ttccggctcg tatgttgtgt ggaattgtga gcggataaca atttcacaca ggaaacaatt   120
g                                                                   121
```

<210> SEQ ID NO 58
<211> LENGTH: 122
<212> TYPE: DNA
<213> ORGANISM: Artificial Sequence
<220> FEATURE:
<223> OTHER INFORMATION: Artificially muteted promoter derived from Escherichia coli

<400> SEQUENCE: 58

```
gcgcaacgca attaatgtga gttagctcac tcattaggca ccccaggctt tacacttatg    60
cttccggctc gtatgttgtg tggaattgtg agcggataac aatttcacac aggaaacaat   120
tg                                                                  122
```

<210> SEQ ID NO 59
<211> LENGTH: 124
<212> TYPE: DNA
<213> ORGANISM: Artificial Sequence
<220> FEATURE:
<223> OTHER INFORMATION: Artificially muteted promoter derived from Escherichia coli

<400> SEQUENCE: 59

```
gcgcaacgca attaatgtga gttagctcac tcattaggca ccccaggctt tacaccttta    60
tgcttccggc tcgtatgttg tgtggaattg tgagcggata acaatttcac acaggaaaca   120
attg                                                                124
```

<210> SEQ ID NO 60
<211> LENGTH: 125
<212> TYPE: DNA
<213> ORGANISM: Artificial Sequence
<220> FEATURE:
<223> OTHER INFORMATION: Artificially muteted promoter derived from Escherichia coli

<400> SEQUENCE: 60

```
gcgcaacgca attaatgtga gttagctcac tcattaggca ccccaggctt tacacccttt    60
atgcttccgg ctcgtatgtt gtgtggaatt gtgagcggat aacaatttca cacaggaaac   120
aattg                                                               125
```

<210> SEQ ID NO 61
<211> LENGTH: 126
<212> TYPE: DNA
<213> ORGANISM: Artificial Sequence

```
<220> FEATURE:
<223> OTHER INFORMATION: Artificially muteted promoter derived from
      Escherichia coli

<400> SEQUENCE: 61
gcgcaacgca attaatgtga gttagctcac tcattaggca ccccaggctt tacacccttt      60
tatgcttccg gctcgtatgt tgtgtggaat tgtgagcgga taacaatttc acacaggaaa    120
caattg                                                                126

<210> SEQ ID NO 62
<211> LENGTH: 18
<212> TYPE: DNA
<213> ORGANISM: Artificial Sequence
<220> FEATURE:
<223> OTHER INFORMATION: Artificial linker sequence

<400> SEQUENCE: 62
caattgatcg atactagt                                                    18

<210> SEQ ID NO 63
<211> LENGTH: 30
<212> TYPE: DNA
<213> ORGANISM: Artificial Sequence
<220> FEATURE:
<223> OTHER INFORMATION: primer

<400> SEQUENCE: 63
gcggaattcg cgcaacgcaa ttaatgtgag                                       30

<210> SEQ ID NO 64
<211> LENGTH: 44
<212> TYPE: DNA
<213> ORGANISM: Artificial Sequence
<220> FEATURE:
<223> OTHER INFORMATION: primer

<400> SEQUENCE: 64
ggcccaattg cacgtgctct ctctcaatca aatcatggcg accg                       44

<210> SEQ ID NO 65
<211> LENGTH: 40
<212> TYPE: DNA
<213> ORGANISM: Artificial Sequence
<220> FEATURE:
<223> OTHER INFORMATION: primer

<400> SEQUENCE: 65
aacatacgag ccggaagcat gtgtaaagcc tggggtgcct                            40

<210> SEQ ID NO 66
<211> LENGTH: 21
<212> TYPE: DNA
<213> ORGANISM: Artificial Sequence
<220> FEATURE:
<223> OTHER INFORMATION: primer

<400> SEQUENCE: 66
atgcttccgg ctcgtatgtt g                                                21

<210> SEQ ID NO 67
<211> LENGTH: 44
<212> TYPE: DNA
<213> ORGANISM: Artificial Sequence
<220> FEATURE:
<223> OTHER INFORMATION: primer
```

```
<400> SEQUENCE: 67
aacatacgag ccggaagcat aaaggtgtaa agcctggggt gcct                              44
```